(12) United States Patent
Roder

(10) Patent No.: US 8,022,056 B2
(45) Date of Patent: Sep. 20, 2011

(54) COMPOSITIONS AND METHODS FOR THE TREATMENT OF CANCER

(75) Inventor: Hanno Roder, Jacksonville, FL (US)

(73) Assignee: Tautatis, Inc, Cambridge, MA (US)

( * ) Notice: Subject to any disclaimer, the term of this patent is extended or adjusted under 35 U.S.C. 154(b) by 397 days.

(21) Appl. No.: 11/956,841

(22) Filed: Dec. 14, 2007

(65) Prior Publication Data

US 2008/0255087 A1    Oct. 16, 2008

Related U.S. Application Data

(60) Provisional application No. 60/875,013, filed on Dec. 14, 2006.

(51) Int. Cl.
*A61K 31/33* (2006.01)
(52) U.S. Cl. ........ 514/183; 514/359; 514/579; 514/461; 514/211.01
(58) Field of Classification Search ................... 514/183, 514/359, 579, 461, 211.01
See application file for complete search history.

(56) References Cited

U.S. PATENT DOCUMENTS

| | | |
|---|---|---|
| 5,079,248 A | 1/1992 | Cross et al. |
| 6,451,786 B1 | 9/2002 | Hudkins et al. |
| 6,541,468 B1 * | 4/2003 | Roder et al. ........... 514/219 |
| 2002/0107237 A1 | 8/2002 | Saulnier et al. |
| 2004/0220202 A1 | 11/2004 | Jaquith et al. |
| 2005/0171182 A1 | 8/2005 | Briesewitz |
| 2006/0128780 A1 | 6/2006 | Hudkins et al. |
| 2007/0232584 A1 | 10/2007 | Roder |

FOREIGN PATENT DOCUMENTS

| | | |
|---|---|---|
| WO | 97/05140 * | 2/1997 |
| WO | WO-97/05140 A1 | 2/1997 |
| WO | WO-98/07433 A1 | 2/1998 |
| WO | 00/01699 * | 1/2000 |
| WO | WO-2005/117550 A2 | 12/2005 |

OTHER PUBLICATIONS

Patani et al. Chem. Rev., 1996, vol. 96, pp. 3147-3176.*
Brueggemeier et al. Endocrine Reviews, 2005, vol. 26, No. 3, pp. 331-345.*
Ciardiello et al. British Journal of Cancer, Jun. 2006, vol. 94, pp. 1604-1609.*
International Search Report for Application No. PCT/US07/25692, dated Apr. 8, 2008.
Supplementary European Search Report for Application No. 07862970.6, dated Dec. 12, 2009.

* cited by examiner

*Primary Examiner* — James Anderson
(74) *Attorney, Agent, or Firm* — Giulio A. DeConti, Jr.; Brian C. Trinque; Lathrop & Gage LLP

(57) ABSTRACT

The present invention relates to the use of specific compounds related to the indolocarbazole K252a, for the preparation of pharmaceutical compositions for the treatment of various forms of cancer.

7 Claims, 18 Drawing Sheets

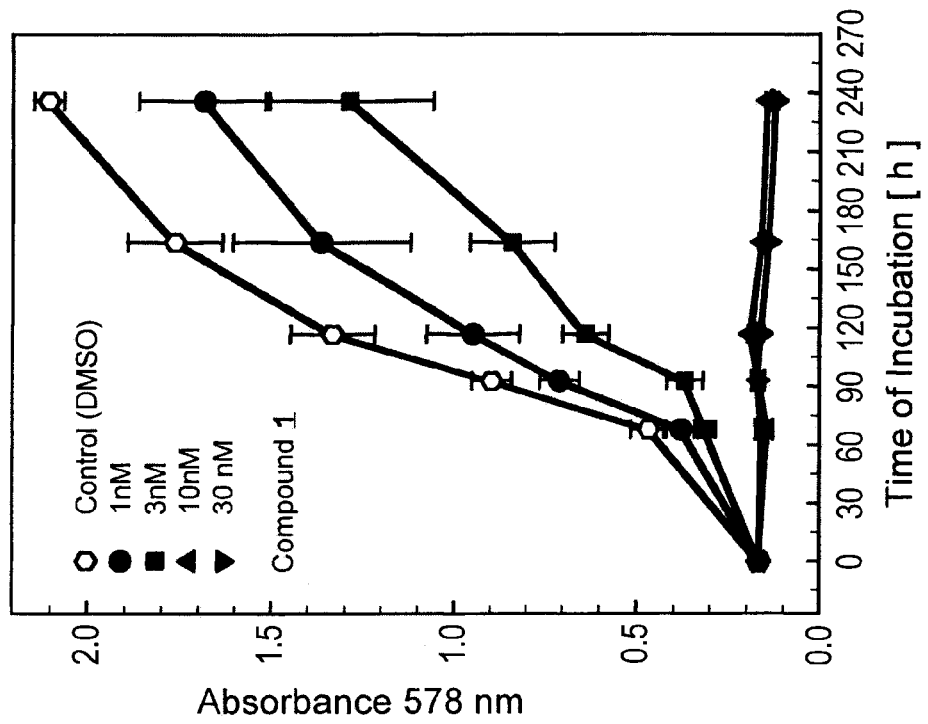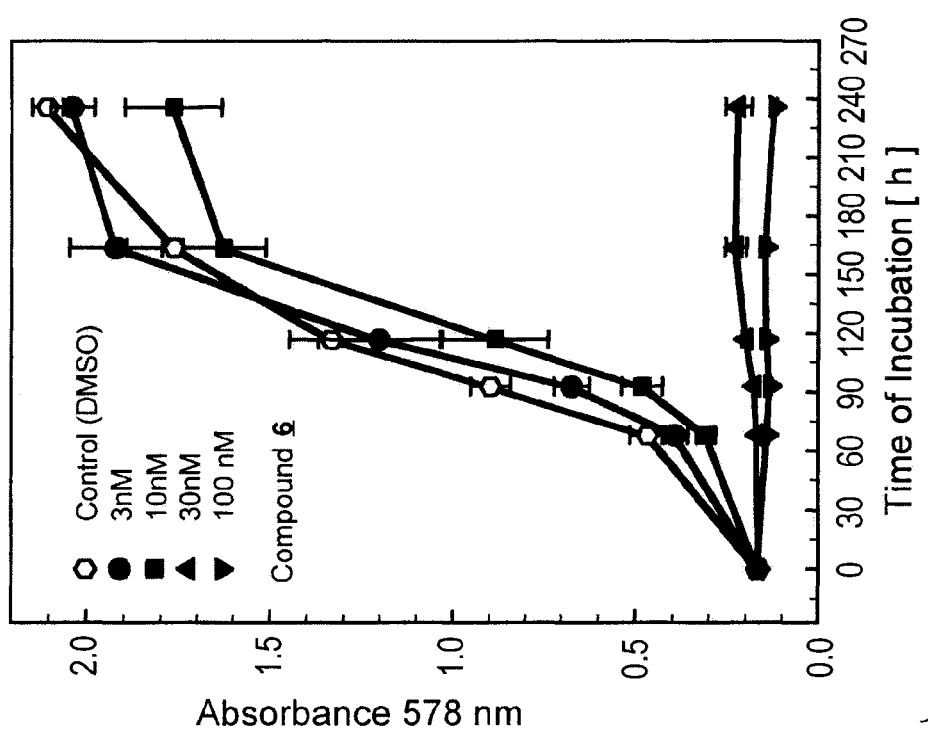
Fig. 3

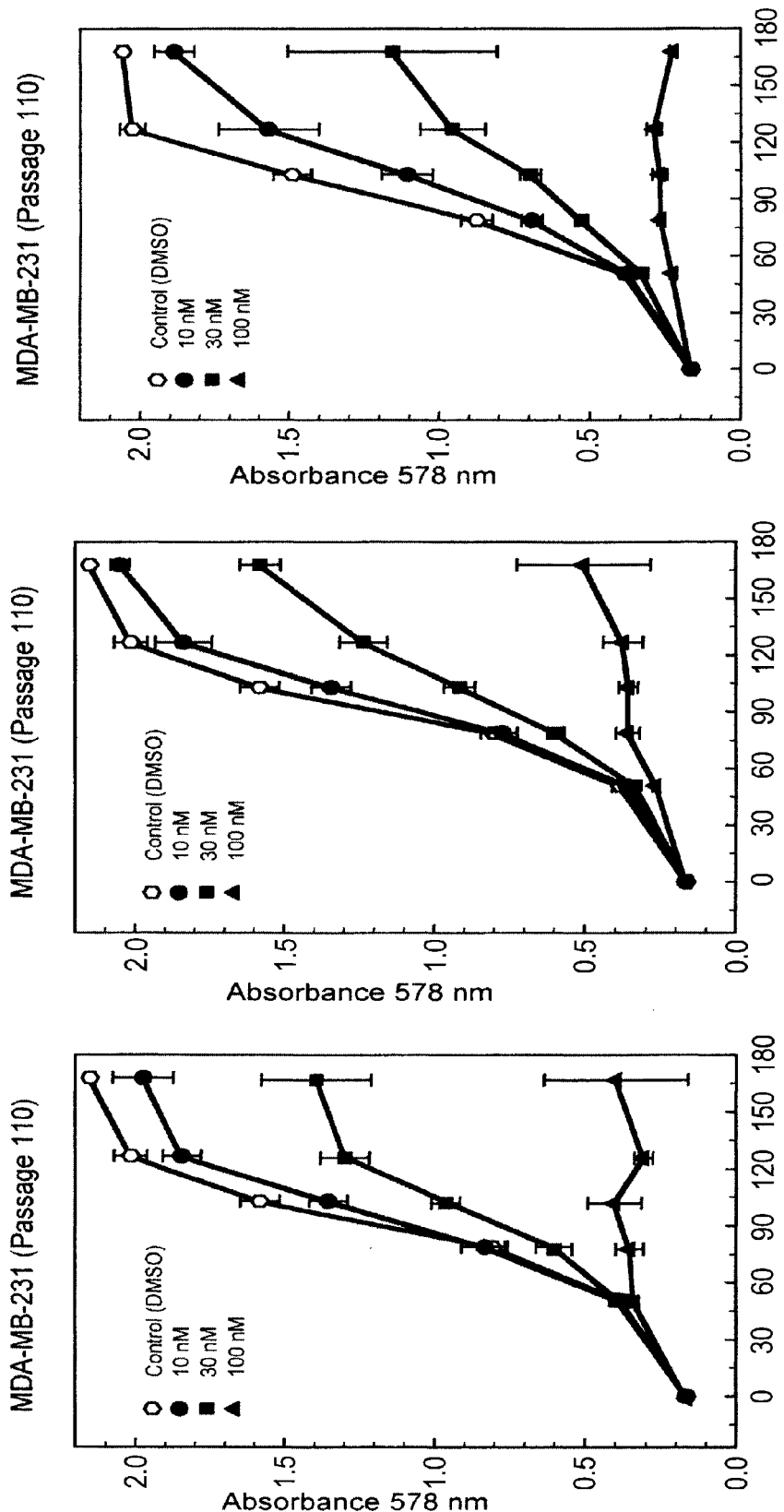

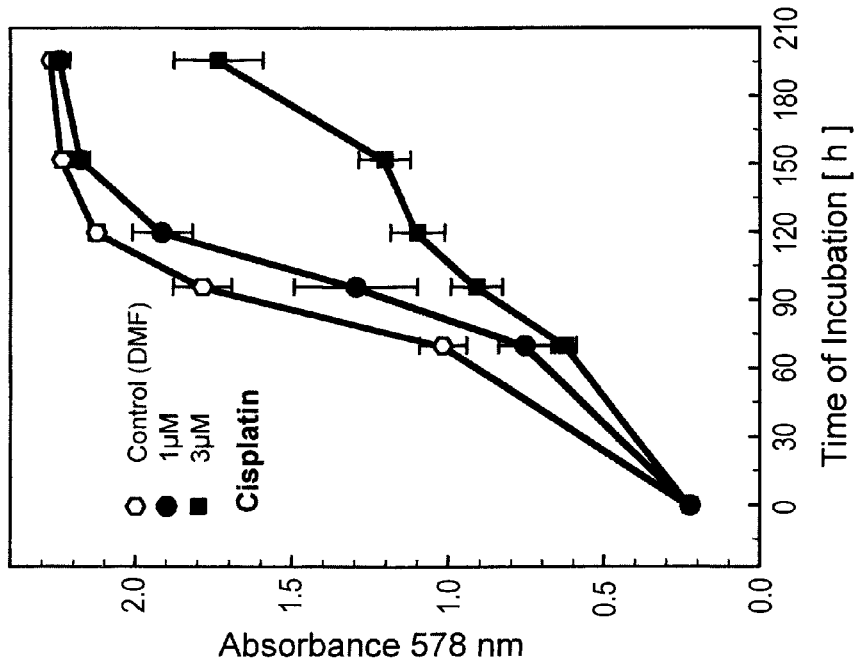
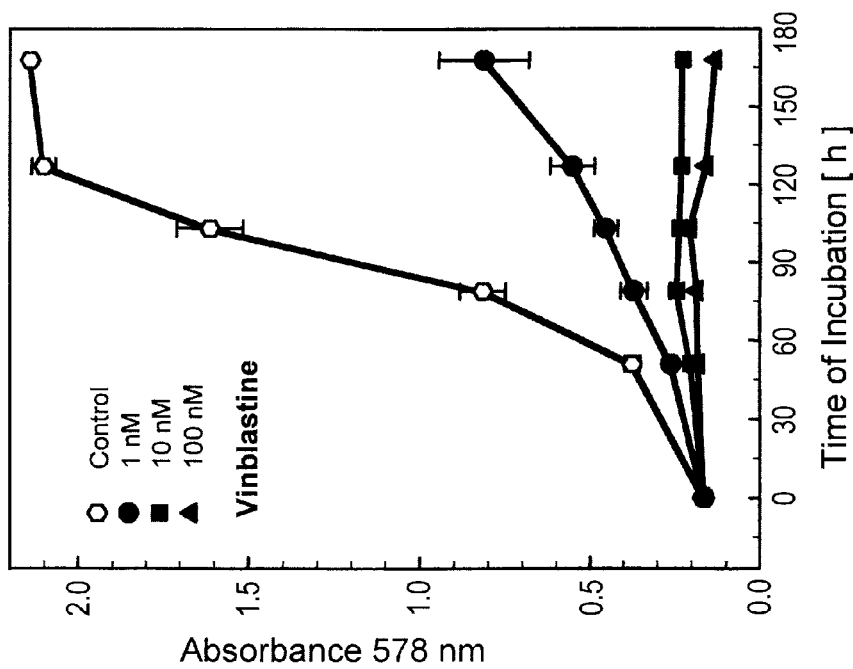
Fig. 5B
Fig. 5A

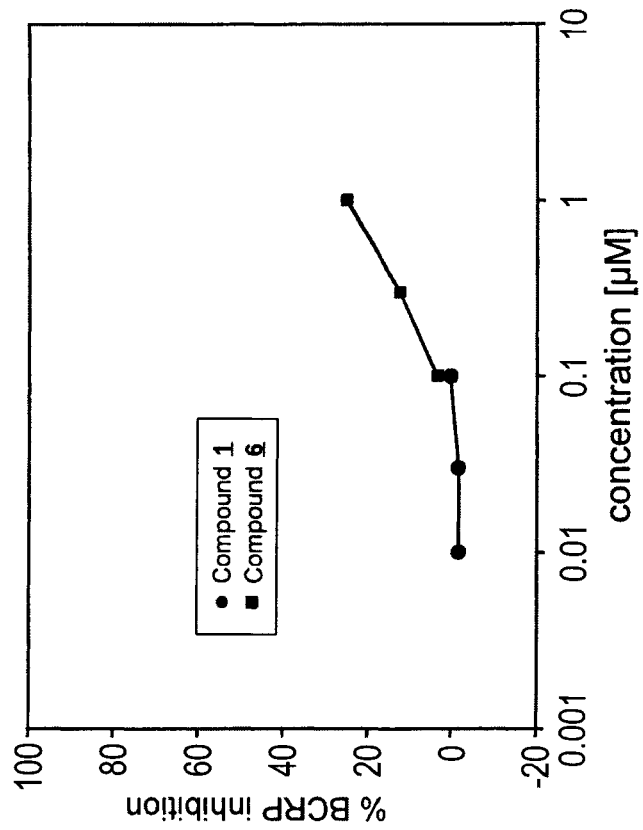
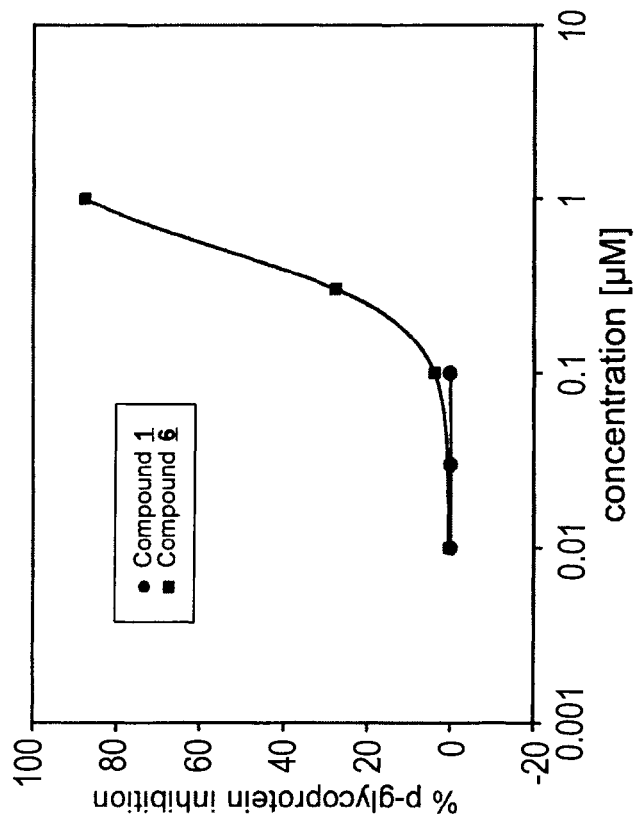
Fig. 6B
Fig. 6A

COMPOSITIONS AND METHODS FOR THE TREATMENT OF CANCER

RELATED APPLICATION

This application claims priority to U.S. Provisional Application No. 60/875,013, filed Dec. 14, 2006, entitled "COMPOSITIONS AND METHODS FOR TREATING CELLULAR PROLIFERATIVE DISEASES." The contents of any patents, patent applications, and references cited throughout this specification are hereby incorporated by reference in their entireties.

FIELD OF THE INVENTION

The present invention relates to the use of specific compounds related to the indolocarbazole K252a, having especially fortuitous pharmaceutical properties, for the preparation of pharmaceutical compositions for the treatment of various forms of cancer.

BACKGROUND OF THE INVENTION

Intracellular phosphorylation events have a decisive impact on the longterm outcome of various pathological conditions by modulating the survival of cells subjected to genetic or environmental insults. In particular, inappropriate activation of certain kinases critically involved in the regulation of the cell cycle, or in the case of postmitotic cells like neurons, in the maintenance of the respective differentiation states, can undermine beneficial physiological responses to a pathological challenge, like apoptosis of cancer cells or neuronal recovery under metabolic stress.

It has become appreciated that certain key kinases, like those belonging to the cell cycle regulated or MAP-kinase superfamilies, are ubiquitously expressed but perform fundamentally different functions in different biological contexts. In proliferating cell types, the physiological activation of such kinases tends to exert a dominant control over cell proliferation, either by synchronizing intracellular events (cdks) or by integrating environmental stimuli and intercellular signals (MAP-kinases). Therefore, intervention on the level of such kinases has therapeutic utility in a variety of cancers.

The involvement of the key MAP-kinase ERK2 and several members of the cdk family in cancer biology is amply documented. Constitutively activated ERK1/2 proteins are a frequent abnormality, e.g., in melanoma cells, often caused by mutation of a membrane receptor coupled to the ERK signal transduction pathways [Abi-Habib et al., Mol. Cancer. Ther. 4, 1303-1310 (2005); Takata et al., J. Invest. Dermatol. 125, 318-322 (2005)]. For most tumor cells with this abnormality, inhibition of the ERK-pathway is toxic. Constitutively activating receptor mutations are a common theme in tumor biology, and a large number of such receptors feed into the ERK pathway. One of the widely known examples are mutations in the signaling molecule ras upstream of the ERK cascade, which account for a sizeable fraction of cancers across the spectrum of originating tissues. Prominent in breast cancer are mutations in the ERB family of tyrosine kinase receptors. However, Tykerb, a new agent used for treatment of Herceptin resistant tumors, shows growth inhibitory activity only in about 20% of a large panel of breast cancer tumor cell lines, in spite of having dual specificity for two ERB receptor subtypes [Konecny et al., Cancer Res. 66, 1630-1639 (2006)]. In contrast, all of the cell lines tested had some level of constitutive ERK2 activity. Thus, intervention on the level of ERK, however, should provide for a more universal therapeutic principle than targeting a myriad of sometimes still unknown upstream receptors with oncogenic mutations [e.g., Zuidervaart et al., Br. J. Cancer 92, 2032-2038 (2005)]. De novo or emerging resistance to other more specific intervention strategies [e.g., Gee et al., Endocr. Relat. Cancer 12 Suppl., S99-S111 (2005)] may also be much less of a problem at the level of ERK2: the homology of ERK2 across mammalian species is virtually absolute, indicating either the absence of mutagenic activity in the respective gene, or a lack of tolerance for any alterations of the protein. Clinical utility of specific interference with ERK activity has recently been demonstrated in patients with advanced malignancies by treatment with an inhibitor of the only known upstream activating kinase of ERKs, termed MEK1/2, thus acting as a proxy for inhibition of ERKs [Lorusso et al., J. Clin. Oncol. 23, 5281-5293 (2005)]. However, even with the clearly very central role of the MAP-kinase pathway in tumor cell transformation, surprising limitations of efficacy of highly specific inhibitors of MEK1/2, and thereby ERK2, have become apparent. While such inhibitors are quite effective in raf-transformed cells, they were shown to loose efficacy in tumor cells harboring oncogenic ras-mutations [Solit et al., Nature 439, 358-362 (2006)], where apparently another pathway besides the MAP-kinase cascade is utilized to provide sufficient transforming activity. This is particularly serious in view of the fact that more than 50% of all known tumors include oncogenic mutations of Ras, thereby providing ample opportunity for unpredictable efficacy or emergence of resistance in recurrent tumors.

There is an urgent need for more broadly acting inhibitors, addressing the ERK pathway, but also preventing the by-pass observed in a majority of clinical cancers. Such inhibitors should finally show the broad therapeutic utility in cancers presenting a broad spectrum of molecular oncogenic mechanisms, and thereby affect the clinically most important outcome of patient survival.

SUMMARY OF THE INVENTION

In its many embodiments, the invention provides specific indolocarbazole derivatives that are inhibitors of a combination of growth-related pathways, methods of preparing such compounds, pharmaceutical compositions comprising one or more such compounds, methods of preparing pharmaceutical formulations comprising one or more such compounds and methods of treatment, prevention, inhibition or amelioration of one or more proliferative diseases such as cancer.

Thus, this invention provides compounds of Formula 1, 2, 3 or 4:

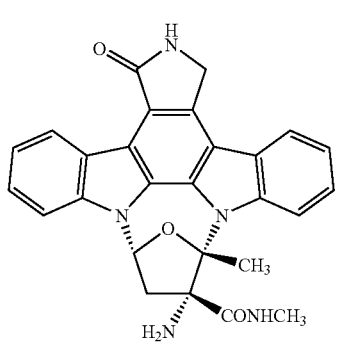

1

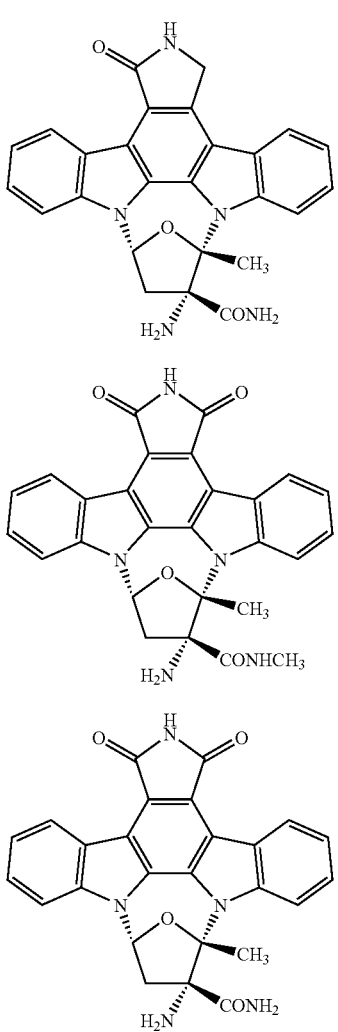

or the pharmaceutically acceptable salts thereof.

This invention also provides a pharmaceutical composition comprising an effective amount of a compound of Formula 1, 2, 3 or 4 and a pharmaceutically acceptable carrier.

The compounds of Formula 1, 2, 3 and 4: (1) potently inhibit growth-related kinase pathways in vitro; (2) have little or no effect inhibitory effect on GSK3 and second messenger kinases (e.g., PKC and PKA) as well as a variety of other kinases in vitro; (3) inhibit abnormal cell growth in most human tumor cell lines, including those which proliferate independent of hormone/growth-factor stimulation (e.g., MDA-MB-231 and U373); (4) are not recognized by drug efflux transporters (MDR proteins), e.g., ABC-G2 (gp170) and ABC-B1 (BCRP); and (5) provide relatively high potency and/or reduced toxicity as compared to conventional anti-cancer agents (e.g., paclitaxel, cisplatin, and related agents).

Thus, this invention further provides a method of inhibiting oncogenic kinase pathways in mammals, especially humans, by the administration of an effective amount of the indolocarbazole compounds described above. The administration of the compounds of Formula 1, 2, 3 or 4 to patients, to inhibit such kinase pathways, is useful in the treatment of the cancers described herein.

This invention also provides methods for (1) inhibiting or treating the abnormal growth of cells, including transformed cells, by administering an effective amount of a compound of Formula 1, 2, 3 or 4; (2) inhibiting or treating tumor growth by administering an effective amount of a compound of Formula 1, 2, 3 or 4 to a mammal (e.g., a human) in need of such treatment; (3) inhibiting or treating the growth of tumors expressing an activated kinase pathway (e.g., ERK1,2) by the administration of an effective amount of a compound of Formula 1, 2, 3 or 4. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), stomach cancer, esophageal cancers, brain cancers, bone cancers, colon cancers (e.g., colorectal carcinomas, such as, for example, colon adenocarcinoma and colon adenoma), myeloid leukemias (for example, acute myelogenous leukemia (AML), lymphomas (e.g. anaplastic large cell lymphoma and other non-Hodgkins lymphomas), thyroid follicular cancer, myelodysplastic syndrome (MDS), bladder carcinoma, renal carcinomas, liver carcinomas, epidermal carcinoma, melanoma, breast cancer and prostate cancer.

In one aspect, the invention provides a method for treating an abnormal growth of cells in a subject in need of such treatment, comprising administering to said subject an effective amount of a compound of Formula 1, 2, 3 or 4, or pharmaceutically acceptable salts thereof.

In another aspect, the invention provides a method of treating tumors expressing elevated levels of an activated kinase pathway (e.g., ERK1,2) in a subject in need of such treatment, comprising administering to said subject an effective amount of a compound of Formula 1, 2, 3 or 4, or pharmaceutically acceptable salts thereof.

In another aspect, the invention provides a method of inhibiting an activated kinase pathway (e.g., ERK1,2) in a subject in need of such treatment comprising administering to said subject an effective amount of a compound of Formula 1, 2, 3 or 4, or pharmaceutically acceptable salts thereof.

In another aspect, the invention provides a method of treating cancer in a subject in need of such treatment comprising administering to said subject an effective amount of a compound of Formula 1, 2, 3 or 4, or pharmaceutically acceptable salts thereof. In one embodiment, the cancer is selected from the group consisting of: breast cancers, colon cancers, gliomas, melanomas, prostate cancers, ovarian cancers, kidney cancers, bladder cancers, head and neck cancers, bone cancers, epidermal cancers, pancreatic cancers, esophageal cancers, stomach cancers, lung cancers, myeloid leukemias, thyroid follicular tumors, myelodysplastic syndrome, non-Hodgkin's lymphomas, and multiple myelomas. In one embodiment, the cancer is selected from the group consisting of lung cancer, colon cancer, brain cancer, melanoma, ovarian cancer, kidney cancer, prostate cancer and breast cancer. In another embodiment, the cancer is breast cancer, colon cancer, or glioma.

In one embodiment of the invention, the cancer is related to activation of a MAP protein kinase as a result of an oncogenic mutation in a gene encoding a cell surface receptor tyrosine kinase (RTK) or other upstream signaling protein. In another embodiment, the MAP protein kinase is extracellular signal regulated kinase-2 (ERK-2) and/or extracellular signal regulated kinase-1 (ERK-1), and wherein said other upstream signaling protein is a Raf or Ras protein.

In another aspect, the invention provides a method of treating cancer in a subject in need of such treatment comprising:

(1) administering to said subject an effective amount of a compound of Formula 1, 2, 3 or 4, or pharmaceutically acceptable salts thereof; and (2) administering to said subject an effective amount of at least one chemotherapeutic agent and/or radiation;

wherein steps (1) and (2) are performed concurrently or sequentially.

In one embodiment, said chemotherapeutic agent is an antineoplastic agent, and wherein said antineoplastic agent is selected from the group consisting of: taxanes; platinum coordinator compounds; EGF inhibitors; VEGF inhibitors; ALK inhibitors, ABL-kinase inhibitors; FLT-kinase inhibitors; MEK-inhibitors, Raf-kinase inhibitors; estrogen receptor antagonists or selective estrogen receptor modulators; anti-tumor nucleoside derivatives; epothilones; topoisomerase inhibitors; vinca alkaloids; inhibitors of alpha-integrins; folate antagonists; ribonucleotide reductase inhibitors; anthracyclines; 17-allylamino-17-demethoxygeldanamycin; biologics; and Thalidomide or a derivative thereof.

In another embodiment, the method comprises administering at least two antineoplastic agents, wherein said at least two antineoplastic agents are taxane and a platinum coordinator compound. In still another embodiment, (a) said taxane is paclitaxel and said platinum coordinator compound is carboplatin; or (b) said taxane is paclitaxel and said platinum coordinator compound is cisplatin; or (c) said taxane is docetaxel and said platinum coordinator compound is cisplatin; or (d) said taxane is docetaxel and said platinum coordinator compound is carboplatin. In yet another embodiment, said antineoplastic agent is selected from the group consisting of: HERCEPTIN® (Trastuzumab), Cetuximab, TYKERB®, TARCEVA®, IRESSA®, bevacizumab, IMC-1C11, SU5416, and SU6688.

In another aspect, the invention provides a method of treating breast cancer in a subject in need of such treatment, comprising administering to said subject a therapeutically effective amount of a compound of Formula 1, 2, 3 or 4, or pharmaceutically acceptable salts thereof; and a therapeutically effective amount of at least one antihormonal agent, wherein said antihormonal agent is selected from the group consisting of aromatase inhibitors, antiestrogens, and LHRH analogues; and wherein said treatment optionally includes the administration of at least one chemotherapeutic agent. In one embodiment, said treatment comprises the administration of a chemotherapeutic agent selected from the group consisting of: Trastuzumab, Lapatinib, Gefitinib, Erlotinib, Bevacizumab, Cetuximab, and Bortezomib.

In another aspect, the invention provides a pharmaceutical composition comprising (1) a compound of Formula 1, 2, 3 or 4, or pharmaceutically acceptable salts thereof; (2) at least one antihormonal agent; and (3) a pharmaceutically acceptable carrier. In one embodiment, the pharmaceutical composition further comprises at least one chemotherapeutic agent.

In one embodiment of any of the methods of treatment described herein, the subject is human.

In another aspect, the invention provides a kit comprising;

(a) a pharmaceutical composition comprising tablets, each comprising a compound of Formula 1, 2, 3 or 4, and a pharmaceutically acceptable carrier, (b) a packaging material enclosing said pharmaceutical composition, and (c) instructions for use of said pharmaceutical composition in the treatment of cancer in a subject in need thereof.

The compounds of Formula 1, 2, 3 or 4 useful in the methods of this invention inhibit or treat the abnormal growth of cells. Without wishing to be bound by theory, it is believed that these compounds may function by selective inhibition of a limited set of central oncogenic pathways, rather than through inhibition of a single initial oncogenic mechanism. In other words, and again without wishing to be bound by theory, it is believed that these compounds may function by inhibiting certain aspects of oncogenic pathways which function independent of constitutive receptor activation, thus making them useful for long-term cancer therapy. Due to a fortuitous combination of potency, selectivity profile, pharmacokinetic properties, and solubility compounds of Formula 1, 2, 3 and 4 are particularly useful in the treatment of drug-resistant forms of cancer, where traditional therapies have failed or are no longer effective.

In another aspect, the invention provides a process for converting compound 6 to compound 1, comprising reacting compound 6 with KCN and $CH_3NH_2$ to form compound 1.

BRIEF DESCRIPTION OF THE DRAWINGS

FIG. 3 shows growth curves for the HT29 colon cancer cell line (Example 4) at increasing concentrations of compound 1, compared to the less potent known compound 6.

FIG. 4 shows the prolonged effect on growth of the MDA-MB-231 breast cancer cell line after a single exposure to various concentrations of compound 1 for limited times of (A) 1 hr, (B) 3 hrs, and (C) 6 hrs.

FIG. 5 shows the effect of increasing concentrations of established anti-cancer agents vinblastine (A) and cis-platin (B) on the growth of the MDA-MB-231 breast cancer cell line.

FIG. 6 compares the recognition of compound 1 and of the compound 6 by two frequently involved multi-drug resistance proteins ABC-B1 (glycoprotein gp170) (A), and ABC-G2 (breast cancer resistance protein BCRP) (B). Measurements were based on competition with the MDR-driven efflux of calcein-AM in Kb-V1 cells expressing high levels of gp170, or competition with the efflux of mitoxandrone in MCF-7 cells by the respective compounds within their effective concentration range. Uptake of fluorescent reporter compounds by competition with 1 or 6 was assessed by FACS as described in Mueller et al., *Cancer Chemother. Pharmacol.* 59, 157-164 (2007).

DETAILED DESCRIPTION OF THE INVENTION

Definitions

Figure 1:
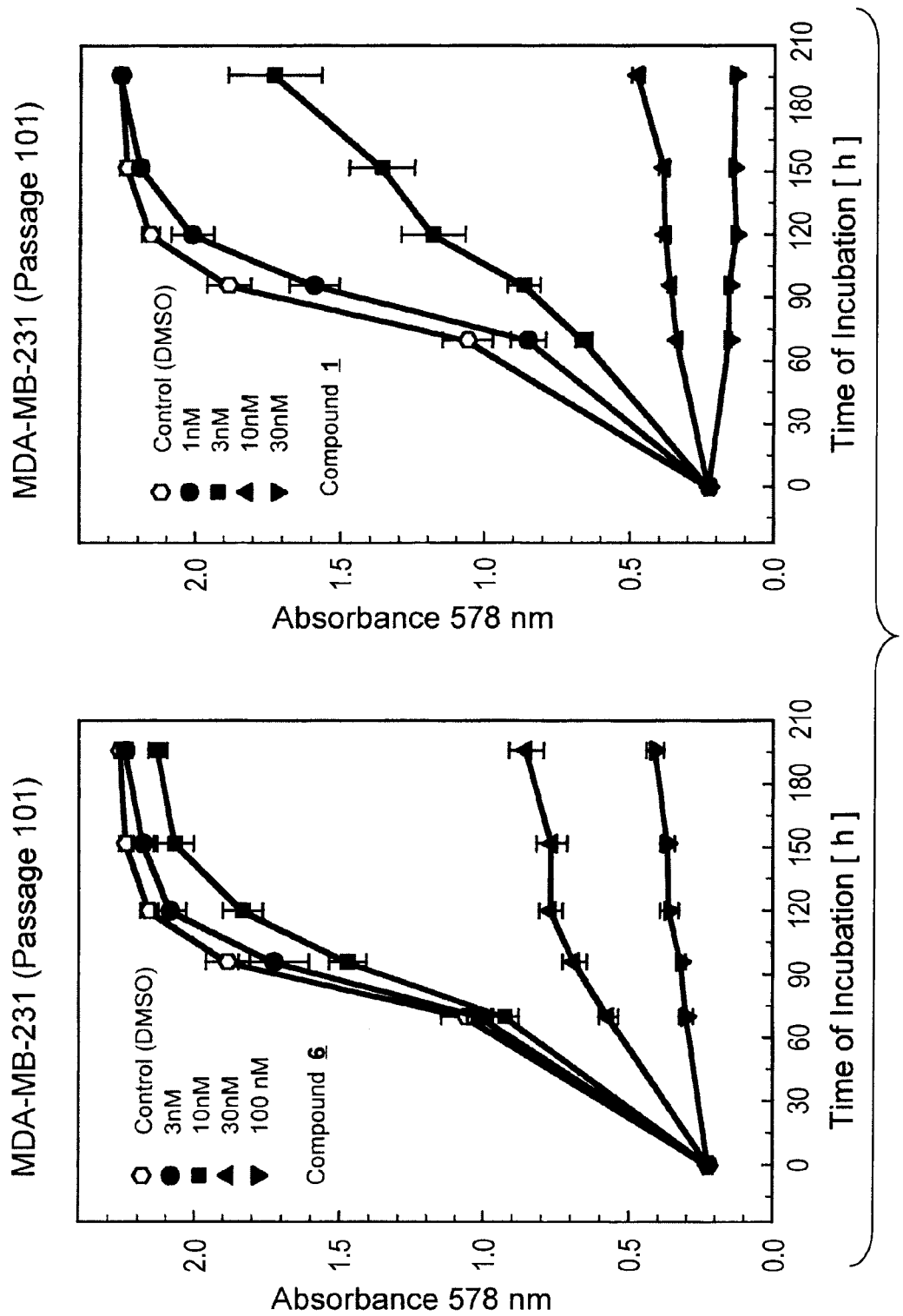
FIG. 1 shows growth curves for the MDA-MB-231 breast cancer cell line at increasing concentrations of compound 1, compared to the less potent known compound 6. Cell densities were measured by the crystal violet staining method as described in Example 3.

As used herein, the following terms are used as defined below unless otherwise indicated:

"Anti-cancer agent", "chemotherapeutic agent", and "antineoplastic agent" have the same meaning, and these terms represent the drugs (medicaments) used to treat cancer.

"Antineoplastic agent" represents a chemotherapeutic agent effective against cancer.

"At least one" means one or more than one, e.g., 1, 2 or 3, or 1 or 2, or 1.

"Compound", with reference to the antineoplastic agents, includes the agents that are antibodies.

"Concurrently" represents (1) simultaneously in time (e.g., at the same time); or (2) at different times during the course of a common treatment schedule.

"Consecutively" means one following the other.

"Different", as used in the phrase "different antineoplastic agents", means that the agents are not the same compound or structure; preferably, "different" as used in the phrase "different antineoplastic agents" means not from the same class of antineoplastic agents; for example, one antineoplastic agent is a taxane, and another antineoplastic agent is a platinum coordinator compound.

"Effective amount" or "therapeutically effective amount" is meant to describe an amount of compound or a composition of the present invention effective in inhibiting or treating the cancer, or effective in inhibiting an extracellular signal-regulated kinase (ERK). For example, the amount of the compound or composition that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, a therapeutically effective amount of the ERK inhibitor is that amount which results in the reduction of ERK activity; the reduction in ERK activity may be determined by the analysis of pharmacodynamic markers such as ERK-1 and cdk-1, using techniques well known in the art.

"One or more" means at least one, e.g., 1, 2 or 3, 1 or 2, or 1.

"Patient" includes humans and animals (preferably, humans).

"Prodrug" represents compounds that are rapidly transformed, for example, by hydrolysis in blood, in vivo to the parent compound, i.e., to the compounds of Formula 1, 2, 3 or 4 or to a salt and/or to a solvate thereof. (See T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.) This invention includes prodrugs of the compounds of Formula 1, 2, 3 or 4.

Sequentially means (1) administration of one component of the method ((a) compound of the invention, or (b) chemotherapeutic agent, signal transduction inhibitor and/or radiation therapy) followed by administration of the other component or components; after administration of one component, the next component can be administered substantially immediately after the first component, or the next component can be administered after an effective time period after the first component; the effective time period is the amount of time given for realization of maximum benefit from the administration of the first component.

"Solvate" means a physical association of a compound of Formula 1, 2, 3 or 4 with one or more solvent molecules; This physical association involves varying degrees of ionic and covalent bonding, including hydrogen bonding; In certain instances the solvate will be capable of isolation, for example when one or more solvent molecules are incorporated in the crystal lattice of the crystalline solid; "Solvate" encompasses both solution-phase and isolatable solvates; Non-limiting examples of suitable solvates include ethanolates, methanolates, and the like; "Hydrate" is a solvate wherein the solvent molecule is $H_2O$.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforementioned "more than one pharmaceutically active agents." The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

As used herein, the term "composition" is intended to encompass a product comprising the specified ingredients in the specified amounts, as well as any product which results, directly or indirectly, from combination of the specified ingredients in the specified amounts.

The term "subject" is intended to include animals, which are capable of suffering from or afflicted with a disease disclosed herein (e.g., cancer), or any disorder involving, directly or indirectly, gated ion channel activity. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer.

Compounds of the Invention

The present invention provides four specific compounds 1-4 out of the broad scope of patent application WO97/05140 (incorporated herein by reference in its entirety), which are distinguished by extraordinary potency and were found to have a unique profile to solve the posed problems and improve significantly on other known compounds, especially the ineffective derivatives exemplified in WO97/05140.

The compounds of the invention are of the Formula 1, 2, 3 or 4:

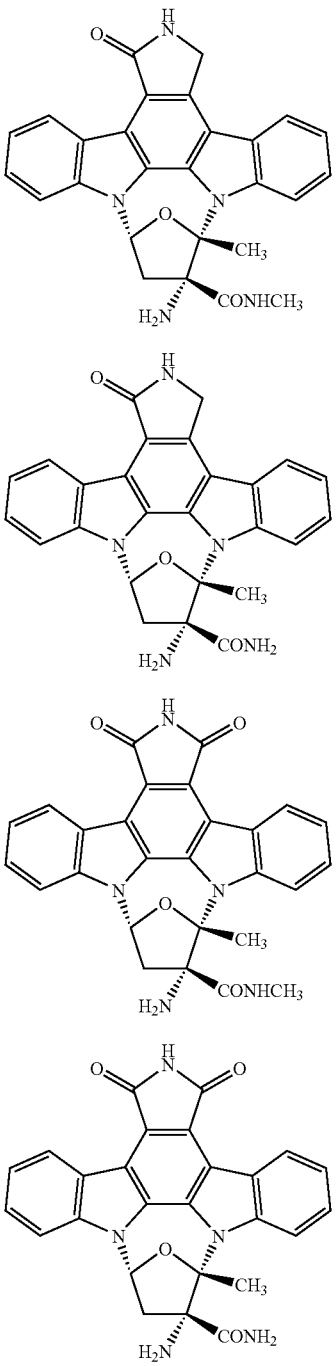

and pharmaceutically acceptable salts thereof.

WO97/05140 discloses a large number of K252a related compounds for the treatment of cancer and immune disorders. However, the unique specific utility of compounds 1-4 in the treatment of cancer, in contrast to the preferred compounds and all other structures in the scope provided by WO97/05140, which are generally ineffective, has not been recognized. As demonstrated by the biological data disclosed herein, the specific compounds of the invention are at least one order of magnitude more potent for the desired anti-tumor activity and have a superior spectrum selectivity than related glycosylated indolocarbazoles disclosed in WO00/01699 and WO04/048384 (both of which are incorporated herein by reference in their entirety), which are less potent and also inhibit PKA, PKC, GSK3 and other kinases at concentrations needed for anti-proliferative activity, and are thus less effective for the treatment of cancers and have a lower therapeutic index. In a preferred embodiment, the compound of the invention is the compound 1.

The compounds of Formula 1, 2, 3 or 4 can form salts that are also within the scope of this invention. Reference to a compound of Formula 1, 2, 3 or 4 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1, 2, 3 or 4 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the Formula 1, 2, 3 or 4 may be formed, for example, by reacting a compound of Formula 1, 2, 3 or 4 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

One or more compounds of Formula 1, 2, 3 or 4 can also exist as, or optionally converted to, a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS Pharm Sci Tech., 5(1), article 12 (2004); and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

Compounds of Formula 1, 2, 3 or 4, and salts, solvates and prodrugs thereof, may exist in their tautomeric form (for example, as an amide or imino ether). All such tautomeric forms are contemplated herein as part of the present invention.

Compounds of Formula 1, 2, 3 or 4 exist in different isomeric (e.g., enantiomers, diastereoisomers, atropisomers) forms. The active compounds of this invention have the absolute and relative configuration of the natural product (+)-K252a.

Polymorphic forms of the compounds of Formula 1, 2, 3 or 4, and of the salts, solvates and prodrugs of the compounds of Formula 1, 2, 3 or 4, are intended to be included in the present invention.

Synthesis compounds useful in this invention are exemplified by the process schemes and examples described herein. These process schemes and examples should not be construed to limit the scope of the disclosure. Alternative mechanistic pathways and analogous structures within the scope of the invention may be apparent to those skilled in the art.

Methods of Treatment

This invention provides a method for inhibiting or treating the abnormal growth of cells, including transformed cells, by administering an effective amount (e.g., a therapeutically effective amount) of one or more (e.g., one) compounds of Formula 1, 2, 3 or 4. Abnormal growth of cells refers to cell growth independent of normal regulatory mechanisms (e.g., loss of contact inhibition). This includes, but is not limited to, the abnormal growth of tumor cells (tumors), both benign and malignant.

This invention also provides a method for inhibiting or treating tumor (i.e., cancer) growth by administering an effective amount (e.g., a therapeutically effective amount) of one or more (e.g., one) compounds of Formula 1, 2, 3 or 4 to a patient in need of such treatment. In another embodiment, this invention provides a method for inhibiting or treating the growth of tumors expressing an activated oncogenic pathway by the administration of an effective amount (e.g., a therapeutically effective amount) of one or more (e.g., one) compounds of Formula 1, 2, 3 or 4.

Examples of proliferative diseases (e.g., tumors, i.e., cancers) that may be inhibited or treated include, but are not limited to: lung cancer (e.g., lung adenocarcinoma and non small cell lung cancer); pancreatic cancers (e.g., pancreatic carcinoma such as, for example, exocrine pancreatic carcinoma); stomach cancers, esophageal cancers, colon cancers (e.g., colorectal carcinomas, such as, for example, colon adenocarcinoma and colon adenoma); myeloid leukemias (for example, acute myelogenous leukemia (AML), CML, and CMML); thyroid follicular cancer; myelodysplastic syndrome (MDS); bladder carcinoma; epidermal carcinoma; melanoma; breast cancer; prostate cancer; head and neck cancers (e.g., squamous cell cancer of the head and neck); ovarian cancer; brain cancers (e.g., gliomas); cancers of mesenchymal origin (e.g., fibrosarcomas and rhabdomyosarcomas sarcomas; tetracarcinomas; neuroblastomas;) bone cancer, kidney carcinomas; hepatomas; Non-Hodgkin's lymphoma; multiple myeloma); and anaplastic thyroid carcinoma.

For example, embodiments of this invention include methods of treating cancer, wherein said cancer is selected from the group consisting of: pancreatic cancers, stomach cancers, esophageal cancers, lung cancers, myeloid leukemias, thyroid follicular tumors, myelodysplastic syndrome, head and neck cancers, melanomas, breast cancers, prostate cancers, ovarian cancers, bladder cancers, gliomas, epidermal cancers, colon cancers, non-Hodgkin's lymphomas, and multiple myelomas, comprising administering to said subject in need of such treatment, an effective amount of one or more (e.g., one) compounds of Formula 1, 2, 3 or 4.

Also for example, embodiments of this invention include methods of treating cancer, wherein said cancers are selected from the group consisting of: lung cancer (e.g., non-small cell lung cancer), head and neck cancer (e.g., squamous cell cancer of the head and neck), bladder cancer, breast cancer, prostate cancer, and myeloid leukemias (e.g., CML and AML), non-Hodgkin's lymphoma and multiple myeloma, comprising administering to said subject in need of such treatment, an effective amount of one or more (e.g., one) compounds of Formula 1, 2, 3 or 4.

In particular embodiments, the compounds of the Formula 1, 2, 3 and 4 can be used to treat breast cancer, colon cancer, prostate cancer, lung cancer, liver cancer, kidney cancer, brain cancer, melanoma, ovarian cancer, stomach cancer, pancreatic cancer, esophageal cancer, throat cancer, bone cancer, and lymphoma in a subject in need thereof.

In other embodiments, the compounds of the Formula 1, 2, 3 and 4 can be used to treat leukemias (e.g., acute myeloid leukemia (AML), and chronic myeloid leukemia (CML), non-Hodgkin's lymphoma, multiple myeloma in a subject in need thereof.

In one embodiment, a compound of Formula 1, 2, 3, and 4 is used to treat lung cancer, colon cancer, brain cancer, melanoma, ovarian cancer, kidney cancer, prostate cancer or breast cancer in a subject in need thereof. In another embodiment, the compound of formula 1 is used to treat lung cancer, colon cancer, brain cancer, melanoma, ovarian cancer, kidney cancer, prostate cancer or breast cancer in a subject in need thereof.

In a preferred embodiment, the subject is human.

This invention provides methods for inhibiting or treating proliferative diseases, particularly established or drug-resistant cancers, independent of the initial oncogenic mechanism. Thus, a MAP kinase may be activated as a result of oncogenic mutation in a gene encoding an upstream signaling protein or over-expression of an oncogene. For example, the upstream signaling protein may be a cell surface receptor tyrosine kinase (RTK), and the MAP kinase activation may be due to mutation or overexpression of tyrosine kinase oncogenes (e.g., neu, src, abl, lck, met, and fyn). Without wishing to be bound by theory, regardless of the initial oncogenic mechanism, the compounds of Formula 1, 2, 3 or 4 selectively inhibit a selected subset of downstream effector pathways, thus making them useful for treating a broad range of proliferative diseases, including forms of cancer resistant to targeted drug treatment.

The compounds of Formula 1, 2, 3 or 4 useful in the methods of this invention inhibit or treat the abnormal growth of cells. Without wishing to be bound by theory, it is believed that these compounds may function through the inhibition of a specific subset of oncogenic pathways, (including ERK-1/2).

Methods of Administration

The compounds of Formula 1, 2, 3 or 4 can be administered orally, preferably as a solid dosage form, more preferably a capsule, and while the total therapeutically effective daily dose can be administered in one to four, or one to two divided doses per day, generally, the therapeutically effective dose is given once or twice a day, preferably twice a day. Examples of dosages for the compounds of Formula 1, 2, 3 or 4 include but are not limited to: about 50 to about 500 mg once per day, about 50 to about 500 mg twice a day, about 50 mg to about 200 mg twice a day, about 75 mg to about 125 mg administered twice a day, or about 100 mg administered twice a day.

If the patient is responding, or is stable, the therapy cycle can be prolonged for an indeterminate period of time according to the judgment of the skilled clinician. The patient can be continued on the compounds of Formula 1, 2, 3 or 4 at the same dose that was administered initially, or, the dose can be adjusted depending on the observed therapeutic benefit ratio in the judgement of a skilled clinician. This maintenance dose can be continued until the patient progresses or can no longer tolerate the dose (in which case the dose can be reduced and the patient can be continued on the reduced dose).

Human patients diagnosed with cancer at any stage can be treated either solely with compounds of the formulas 1-4, or in combination with other established treatment regimen, including but not limited to platin-based compounds, taxol and other similarly acting microtubule stabilizing or disrupting compounds, other kinase inhibitors, radiation therapy and various cocktails including drugs to ameliorate the side effects of such treatments, such as anti-emetics and steroids. Combination treatment is especially indicated with other molecularly targeted agents, including but not limited to tyrosine kinase inhibitors, such as TYKERB®, TARCEVA®, IRESSA®, etc., and monoclonal antibodies, such as HERCEPTIN® (Trastuzumab). Treatment with compounds of the formula 1-4 is especially indicated in cases where receptor-targeted therapies are exhausted, or conventional chemotherapeutic regimen are no longer effective or too toxic for the patient. The compounds of the formulas 1-4 are preferentially given as oral dosages of 0.1-10 mg/kg, either once or twice daily, or on a weekly schedule, depending on tumor responses monitored by imaging methods (e.g. CAT scan, MRI), or in certain cases by measuring the level of circulating tumor antigens. Higher and more frequent dosing is preferred for treatment of established solid tumors and metastasized tumors, while the lower and less frequent doses can be employed to prevent recurrence after remission, or in a prophylactic mode where certain tumor markers are detectable without manifest tumors. In particularly serious cases the compounds of the formula 1-4 can also be administered intravenously in vehicles designed to enhance solubility (e.g., polyvinyl pyrrolidone or polyethylene glycols) to approach maximal tolerated plasma concentrations under clinical supervision for maximal effect. Thereafter patients may be switched to oral maintenance dosing.

The compounds of the formulas 1-4 can also be administered by alternate routes, such as subcutaneously, parenterally (e.g. colon cancer), transdermally (e.g. skin tumors), or by inhalation of sprays (e.g. lung cancer).

The pharmaceutical compositions for oral dosage forms of compounds of the formulas 1-4 may include a variety of inactive adjuvant substances in tablets or capsules, to aid the dissolution of the compounds or modulate the timing of their release (e.g. in extended release formulations). Such ingredients may include but are not limited to high molecular weight polyethylene glycols or polyvinyl pyrrolidones (Povidone), which may preferably be formulated with compounds of the formulas 1-4 in solid dispersions to enhance gastrointestinal solubility and/or dissolution rate. Compounds of the formulas 1-4 may also be administered orally in form of solutions containing GRAS (Generally Regarded As Safe) vehicle components to aid dissolution, including but not limited to low molecular weight polyethylene glycols (PEGs), polyvinyl pyrrolidones, sorbitol, mannitol and similar polyhydroxylated compounds, carboxymethyl cellulose, dextranes, etc. Such dissolution aids may also be employed in liquid formulations for intravenous infusion.

Compounds of the formulas 1-4 can advantageously be administered in salt form to aid their dissolution and resorption. Pharmaceutically acceptable salts include, but are not limited to, chlorides, sulfates, phosphates, and salts of organic acids like acetates, formiates, tosylates, benzoates, salicylates, lactates, malonates, succinates, tartrates, citrates, ascorbates etc.

In another aspect of the present invention, pharmaceutical compositions are provided, which comprise any one of the compounds of the Formulas 1, 2, 3 or 4, (or a prodrug, pharmaceutically acceptable salt or other pharmaceutically acceptable derivative thereof), and optionally comprise a pharmaceutically acceptable carrier. After formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered at dosage levels of about 0.1 mg/kg to about 50 mg/kg, from about 1 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.1 mg/kg or greater than 50 mg/kg can be administered to a subject. In certain embodiments, compounds are administered orally or parenterally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), cremaphor, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. Preferably, polyethylene glycols or polyvinyl pyrrolidone are employed as solubilizing agents.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinyl pyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof, and (j) dissolution rate enhancers like high molecular weight polyethylene glycols or polyvinyl pyrrolidone in physical mixtures or in form of solid dispersions. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Methods of Treatment—Combination Therapies

The present invention also provides a method of treating proliferative diseases, especially cancers (i.e., tumors), comprising administering an effective amount (e.g., a therapeutically effective amount) of one or more (e.g., one) compound of Formula 1, 2, 3, or 4, described herein, to a mammal (e.g., a human) in need of such treatment in combination with an effective amount of at least one anti-cancer agent (i.e., a chemotherapeutic agent) and/or radiation.

Examples of anti-cancer agents (i.e., chemotherapeutic agents) include anti-cancer agents selected from the group consisting of: taxanes, platinum coordinator compounds, epidermal growth factor (EGF) inhibitors that are antibodies, EGF inhibitors that are small molecules, vascular endothelial growth factor (VEGF) inhibitors that are antibodies, VEGF kinase inhibitors that are small molecules, MET inhibitors, ABL kinase inhibitors, ALK inhibitors, FLT-kinase inhibitors, MAPK/ERK kinase (MEK) inhibitors, RAF kinase inhibitors, farnesyl transferase inhibitors, estrogen receptor antagonists or selective estrogen receptor modulators (SERMs), anti-tumor nucleoside derivatives, epothilones, topoisomerase inhibitors, vinca alkaloids, antibodies that are inhibitors of integrins, small molecules that are inhibitors of integrins, folate antagonists, ribonucleotide reductase inhibitors, anthracyclines, biologics; thalidomide (or related imid), heat shock protein 90 inhibitors.

This invention also provides a method of treating cancer in a patient in need of such treatment comprising administering to said patient a therapeutically effective amount of one or more (e.g., one) compounds of compound of Formula 1, 2, 3, or 4, and therapeutically effective amounts of at least two different antineoplastic agents selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) MET inhibitors, (8) ABL kinase inhibitors, (9) ALK inhibitors, (10) FLT-kinase inhibitors, (11) MAPK/ERK kinase (MEK) inhibitors, (12) RAF kinase inhibitors, (13) farnesyl transferase inhibitors, (14) estrogen receptor antagonists or selective estrogen receptor modulators (SERMs), (15) anti-tumor nucleoside derivatives, (16) epothilones, (17) topoisomerase inhibitors, (18) vinca alkaloids, (19) antibodies that are inhibitors of integrins, (20) small molecules that are inhibitors of integrins, (21) folate antagonists, (22) ribonucleotide reductase inhibitors, (23) anthracyclines, (24) biologics; (25) thalidomide (or related imid), (26) heat shock protein 90 inhibitors.

This invention also provides a method of treating cancer in a patient in need of such treatment comprising administering to said patient therapeutically effective amounts of one or more (e.g., one) compounds of compound of Formula 1, 2, 3, or 4, and an antineoplastic agent selected from the group consisting of: (1) EGF inhibitors that are antibodies, (2) EGF inhibitors that are small molecules, (3) VEGF inhibitors that are antibodies, and (4) VEGF inhibitors that are small molecules. Radiation therapy can also be used in conjunction with the above combination therapy, i.e., the above method using a combination of compounds of compound of Formula 1, 2, 3, or 4, and antineoplastic agent can also comprise the administration of a therapeutically effect amount of radiation.

This invention also provides a method of treating leukemias (e.g., acute myeloid leukemia (AML), and chronic myeloid leukemia (CML) in a patient in need of such treatment comprising administering to said patient therapeutically effective amounts of one or more (e.g., one) compounds of Formula 1, 2, 3 or 4 and: (1) Gleevec and interferon to treat CML; (2) Gleevec and pegylated interferon to treat CML; (3) an anti-tumor nucleoside derivative (e.g., Ara-C) to treat AML; or (4) an anti-tumor nucleoside derivative (e.g., Ara-C) in combination with an anthracycline to treat AML.

This invention also provides a method of treating non-Hodgkin's lymphoma in a patient in need of such treatment comprising administering to said patient therapeutically effective amounts of one or more (e.g., one) compounds of compound of Formula 1, 2, 3, or 4, and: (1) a biologic (e.g., Rituxan); (2) a biologic (e.g., Rituxan) and an anti-tumor nucleoside derivative (e.g., Fludarabine); or (3) Genasense (antisense to BCL-2).

This invention also provides a method of treating multiple myeloma in a patient in need of such treatment comprising administering to said patient therapeutically effective amounts of one or more (e.g., one) compounds of compound of Formula 1, 2, 3, or 4, and: (1) a proteosome inhibitor (e.g., Velcade/Bortezumib from Millenium); or (2) Thalidomide (or related imid).

This invention also provides a method of treating cancer, said treatment comprising administering to a patient in need of such treatment therapeutically effective amounts of (a) one or more (e.g., one) compounds of compound of Formula 1, 2, 3, or 4;

(b) at least two different antineoplastic agents selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) MET inhibitors, (8) ABL kinase inhibitors, (9) ALK inhibitors, (10) FLT-kinase inhibitors, (11) MAPK/ERK kinase (MEK) inhibitors, (12) RAF kinase inhibitors, (13) farnesyl transferase inhibitors, (14) estrogen receptor antagonists or selective estrogen receptor modulators (SERMs), (15) anti-tumor nucleoside derivatives, (16) epothilones, (17) topoisomerase inhibitors, (18) vinca alkaloids, (19) antibodies that are inhibitors of integrins, (20) small molecules that are inhibitors of integrins, (21) folate antagonists, (22) ribonucleotide reductase inhibitors, (23) anthracyclines, (24) biologics; (25) thalidomide (or related imid), (26) heat shock protein 90 inhibitors.

Antineoplastic agents that can be used in combination with the kinase inhibitors (i.e. the compounds of compound of Formula 1, 2, 3, or 4) are:

(1) Taxanes such as paclitaxel (TAXOL) and/or docetaxel (Taxotere);

(2) Platinum coordinator compounds, such as, for example, carboplatin, cisplatin and oxaliplatin;

(3) EGF inhibitors that are antibodies, such as: HER2 antibodies (such as, for example trastuzumab (Herceptin), Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), CI 1033 (Pfizer Global Research and Development), trastuzmab-maytansinoid conjugate (Genentech, Inc.), mitumomab (Imclone Systems and Merck KGaA) and Melvax II (Imclone Systems and Merck KgaA);

(4) EGF inhibitors that are small molecules, such as, Tykerb (GSK), Tarceva (OSI-774, OSI Pharmaceuticals, Inc.), and Iressa (ZD 1839, Astra Zeneca);

(5) VEGF inhibitors that are antibodies such as: bevacizumab (Genentech, Inc.), and IMC-1 C11 (ImClone Systems), DC 101 (a KDR VEGF Receptor 2 from ImClone Systems);

(6) VEGF kinase inhibitors that are small molecules such as SU 5416 and SU 6688 (both from Sugen, Inc.);

(7) Estrogen Receptor Antagonists or Selective Estrogen Receptor Modulators (SERMs), such as tamoxifen, idoxifene, raloxifene, trans-2,3-dihydroraloxifene, levormeloxifene, droloxifene, MDL 103,323, and acolbifene (Schering Corp.);

(8) ABL kinase inhibitors such as Gleevec (Novartis);

(9) FLT-kinase inhibitors, such as CEP-701 (Cephalon);

(10) MEK inhibitors such as CI-1040 (Pfizer), AZD 6244 (Array Biopharma);

(11) RAF kinase inhibitors such as Nevaxar/Sorafenib (Bayer/Onyx);

(12) Anti-tumor nucleoside derivatives such as 5-fluorouracil, gemcitabine or capecitabine;

(13) Epothilones such as BMS-247550 (Bristol-Myers Squibb), and EP0906 (Novartis Pharmaceuticals);

(14) Topoisomerase inhibitors such as topotecan (Glaxo SmithKline), and Camptosar (Pharmacia);

(15) Vinca alkaloids, such as, navelbine (Anvar and Fabre, France), vincristine and vinblastine;

(16) Antibodies that are inhibitors of αVβ3 integrins, such as, LM-609 (see, Clinical Cancer Research, Vol. 6, page 3056-3061, August 2000, the disclosure of which is incorporated herein by reference thereto); and

(17) Heat Shock Protein HSP-90 inhibitors, such as 17-Allylamino-17-demethoxygeldanamycin (17-AAG).

Preferred antineoplastic agents are selected from: paclitaxel, docetaxel, carboplatin, cisplatin, oxaliplatin, gemcitabine, tamoxifen, HERCEPTIN® (Trastuzumab), Cetuximab, TYKERB®, Dasatinib, TARCEVA®, IRESSA®, bevacizumab, navelbine, IMC-1C11, SU5416 or SU6688. Most preferred antineoplastic agents are selected from: paclitaxel, docetaxel, carboplatin, cisplatin navelbine, gemcitabine, 17-Allylamino-17-demethoxygeldanamycin (17-AAG), Tykerb, or Herceptin.

This invention is also directed to the methods of treating cancer described herein, particularly those described above, wherein in addition to the administration of the compounds of Formula 1, 2, 3 or 4 and antineoplastic agents, radiation therapy is also administered prior to, during, or after the treatment cycle.

The method of treating proliferative diseases (cancers, i.e., tumors), according to this invention, includes a method for treating (inhibiting) the abnormal growth of cells, including transformed cells, in a patient in need of such treatment, by administering, concurrently or sequentially, an effective amount of one or more (e.g., one) compounds of Formula 1, 2, 3 or 4 and an effective amount of a chemotherapeutic agent and/or radiation.

Other embodiments of the methods of the present invention include methods for treating or inhibiting tumor growth in a patient in need of such treatment by administering, concurrently or sequentially, (1) an effective amount of one or more (e.g., one) compounds of Formula 1, 2, 3 or 4 and (2) an effective amount of at least one antineoplastic agent, microtubule affecting agent and/or radiation therapy. For example, one embodiment of these methods is directed to a method of treating cancers selected from the group consisting of: lung cancer, prostate cancer and myeloid leukemias.

The methods of treating proliferative diseases, according to this invention, also include a method for treating (inhibiting) proliferative diseases, both benign and malignant, by administering, concurrently or sequentially, an effective amount of a compound of Formula 1, 2, 3 or 4 and an effective amount of an antineoplastic agent and/or radiation therapy to a patient in need of such treatment. For radiation therapy, γ-radiation is preferred.

Embodiments of the methods of treatment of this invention are directed to the use of a combination of drugs (compounds) for the treatment of cancer, i.e., this invention is directed to a combination therapy for the treatment of cancer. Those skilled in the art will appreciate that the drugs are generally administered individually as a pharmaceutical composition. The use of a pharmaceutical composition comprising more than one drug is within the scope of this invention.

The antineoplastic agents are usually administered in the dosage forms that are readily available to the skilled clinician, and are generally administered in their normally prescribed amounts (as for example, the amounts described in the Physician's Desk Reference, 57th Edition, 2003 (published by Thompson PDR, Montvale, N.J. 07645-1742 the disclosure of which is incorporated herein by reference thereto), or the amounts described in the manufacture's literature for the use of the agent).

For example, the compounds of Formula 1, 2, 3 or 4 can be administered orally (e.g., as a capsule), and the antineoplastic agents can be administered intravenously, usually as an IV solution. The use of a pharmaceutical composition comprising more than one drug is within the scope of this invention.

The compounds of Formula 1, 2, 3 or 4 and the antineoplastic agents are administered in therapeutically effective dosages to obtain clinically acceptable results, e.g., reduction or elimination of symptoms or of the tumor. Thus, the compounds of Formula 1, 2, 3 or 4 and antineoplastic agents can be administered concurrently or consecutively in a treatment protocol. The administration of the antineoplastic agents can be made according to treatment protocols already known in the art.

The compounds of Formula 1, 2, 3 or 4 and antineoplastic agents are administered in a treatment protocol that usually lasts one to seven weeks, and is repeated typically from 6 to 12 times. Generally the treatment protocol lasts one to four weeks. Treatment protocols of one to three weeks may also be used. A treatment protocol of one to two weeks may also be used. During this treatment protocol or cycle the kinase inhibitor 1, 2, 3, or 4 is administered daily while the antineoplastic agents are administered one or more times a week. Generally, the compounds of Formula 1, 2, 3 or 4 can be administered daily (i.e., once per day), preferably twice per day, and the antineoplastic agent is administered once a week or once every three weeks. For example, the taxanes (e.g., Paclitaxel (e.g., Taxol) or Docetaxel (e.g., Taxotere) can be administered once a week or once every three weeks.

However, those skilled in the art will appreciate that treatment protocols can be varied according to the needs of the patient. Thus, the combination of compounds (drugs) used in the methods of this invention can be administered in variations of the protocols described above. For example, the compounds of Formula 1, 2, 3 or 4 can be administered discontinuously rather than continuously during the treatment cycle. Thus, for example, during the treatment cycle the compounds of Formula 1, 2, 3 or 4 can be administered daily for a week and then discontinued for a week, with this administration repeating during the treatment cycle. Or the compounds of Formula 1, 2, 3 or 4 can be administered daily for two weeks and discontinued for a week, with this administration repeating during the treatment cycle. Thus, the compounds of Formula 1, 2, 3 or 4 can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein the compounds of Formula 1, 2, 3 or 4 are not dosed does not have to equal the number of days (or weeks) wherein the compounds of Formula 1, 2, 3 or 4 are dosed. Usually, if a discontinuous dosing protocol is used, the number of days or weeks that the compounds of Formula 1, 2, 3 or 4 are dosed are at least equal or greater than the number of days or weeks that the compounds of Formula 1, 2, 3 or 4 are not dosed.

The antineoplastic agent could be given by bolus or continuous infusion. The antineoplastic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days, with the pattern repeating during the treatment cycle.

The antineoplastic agents used with the compounds of Formula 1, 2, 3 or 4 are administered in their normally prescribed dosages during the treatment cycle (i.e., the antineoplastic agents are administered according to the standard of practice for the administration of these drugs). For example: (a) about 30 to about 300 mg/m$^2$ for the taxanes; (b) about 30 to about 100 mg/m for Cisplatin; (c) AUC of about 2 to about 8 for Carboplatin; (d) about 2 to about 4 mg/m$^2$ for EGF inhibitors that are antibodies; (e) about 50 to about 500 mg/m$^2$ for EGF inhibitors that are small molecules; (f) about 1 to about 10 mg/m$^2$ for VEGF kinase inhibitors that are antibodies; (g) about 50 to about 2400 mg/m$^2$ for VEGF inhibitors that are small molecules; (h) about 1 to about 20 mg for SERMs; (i) about 500 to about 1250 mg/m$^2$ for the anti-tumor nucleosides 5-Fluorouracil, Gemcitabine and Capecitabine; (j) for the anti-tumor nucleoside Cytarabine (Ara-C) 100-200 mg/m$^2$/day for 7 to 10 days every 3 to 4 weeks, and high doses for refractory leukemia and lymphoma, i.e., 1 to 3 gm/m$^2$ for one hour every 12 hours for 4-8 doses every 3 to four weeks; (k) for the anti-tumor nucleoside Fludarabine (F-ara-A) 10-25 mg/m$^2$/day every 3 to 4 weeks; (I) for the anti-tumor nucleoside Decitabine 30 to 75 mg/m$^2$ for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m$^2$ for epothilones; (o) about 1 to about 350 mg/m$^2$ for topoisomerase inhibitors; (p) about 1 to about 50 mg/m$^2$ for vinca alkaloids; (q) for the folate antagonist Methotrexate (MTX) 20-60 mg/m$^2$ by oral, IV or IM every 3 to 4 weeks, the intermediate dose regimen is 80-250 mg/m$^2$ IV over 60 minutes every 3 to 4 weeks, and the high dose regimen is 250-1000 mg/m$^2$ IV given with leucovorin every 3 to 4 weeks; (r) for the folate antagonist Premetrexed (Alimta) 300-600 mg/m$^2$ (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m$^2$ every 3 to 4 weeks (preferably used for solid tumors such as non-small cell lung cancer, colorectal cancer and ovarian cancer); (u) for the anthracycline daunorubicin 10-50 mg/m$^2$/day IV for 3-5 days every 3 to 4 weeks; (v) for the anthracycline Doxorubicin (Adriamycin) 50-100 mg/m$^2$ IV continuous infusion over 1-4 days every 3 to 4 weeks, or 10-40 mg/m$^2$ IV weekly; (w) for the anthracycline Idarubicin 10-30 mg/m$^2$ daily for 1-3 days as a slow IV infusion over 10-20 minutes every 3 to 4 weeks; (x) for the biologic interferon (Intron-A, Roferon) 5 to 20 million IU three times per week; (y) for the biologic pegylated interferon (Peg-intron, Pegasys) 3 to 4 micrograms/kg/day chronic sub cutaneous (until relapse or loss of activity); and (z) for the biologic Rituximab (Rituxan) (antibody used for non-Hodgkin's lymphoma) 200-400 mg/m$^2$ IV weekly over 4-8 weeks for 6 months.

Gleevec can be used orally in an amount of about 200 to about 800 mg/day.

Thalidomide (and related imids) can be used orally in amounts of about 200 to about 800 mg/day, and can be continuously dosed or used until relapse or toxicity. See for example Mitsiades et al., "Apoptotic signaling induced by immunomodulatory thalidomide analogs in human multiple myeloma cells; therapeutic implications", Blood, 99(12):4525-30, Jun. 15, 2002, the disclosure of which is incorporated herein by reference thereto.

For example, Paclitaxel (e.g., Taxol can be administered once per week in an amount of about 50 to about 100 mg/m$^2$ with about 60 to about 80 mg/m$^2$ being preferred. In another example Paclitaxel (e.g., Taxol can be administered once every three weeks in an amount of about 150 to about 250 mg/m$^2$ with about 175 to about 225 mg/m$^2$ being preferred.

In another example, Docetaxel (e.g., Taxotere) can be administered once per week in an amount of about 10 to about 45. In another example Docetaxel (e.g., Taxotere) can be administered once every three weeks in an amount of about 50 to about 100 mg/m$^2$.

In another example Cisplatin can be administered once per week in an amount of about 20 to about 40 mg/m$^2$. In another example Cisplatin can be administered once every three weeks in an amount of about 60 to about 100 mg/m$^2$.

In another example Carboplatin can be administered once per week in an amount to provide an AUC of about 2 to about 3. In another example Carboplatin can be administered once every three weeks in an amount to provide an AUC of about 5 to about 8.

Antineoplastic agents that can be used in combination with the compounds of Formula 1, 2, 3 or 4 are:

(1) Taxanes such as paclitaxel (TAXOL) and/or docetaxel (Taxotere);

(2) Platinum coordinator compounds, such as, for example, carboplatin, cisplatin and oxaliplatin;

(3) EGF inhibitors that are antibodies, such as: HER2 antibodies (such as, for example trastuzumab (Herceptin, Genentech, Inc.), Cetuximab (Erbitux, IMC-C225, ImClone Systems), EMD 72000 (Merck KGaA), anti-EFGR monoclonal antibody ABX (Abgenix), TheraCIM-h-R$^3$ (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithkline), CI 1033 (Pfizer Global Research and Development), trastuzmab-maytansinoid conjugate (Genentech, Inc.), mitumomab (Imclone Systems and Merck KGaA) and Melvax II (Imclone Systems and Merck KgaA);

(4) EGF inhibitors that are small molecules, such as, Tarceva™ (OSI-774, OSI Pharmaceuticals, Inc.), and Iressa (ZD 1839, Astra Zeneca);

(5) VEGF inhibitors that are antibodies such as: bevacizumab (Genentech, Inc.), and IMC-1C11 (ImClone Systems), DC 101 (a KDR VEGF Receptor 2 from ImClone Systems);

(6) VEGF kinase inhibitors that are small molecules such as SU 5416 and SU 6688 (both from Sugen, Inc.);

(7) Estrogen receptor antagonists or selective estrogen receptor modulators (SERMs), such as tamoxifen, idoxifene, raloxifene, trans-2,3-dihydroraloxifene, levormeloxifene, droloxifene, MDL 103,323, and acolbifene (Schering Corp.);

(8) ABL kinase inhibitors such as Gleevec (Novartis);

(9) FLT-kinase inhibitors, such as CEP-701 (Cephalon);

(10) MEK inhibitors such as CI-1040 (Pfizer), AZD 6244 (Array Biopharma);

(11) RAF kinase inhibitors such as Nevaxar/Sorafenib (Bayer/Onyx);

(12) Anti-tumor nucleoside derivatives such as 5-fluorouracil, gemcitabine or capecitabine;

(13) Epothilones such as BMS-247550 (Bristol-Myers Squibb), and EP0906 (Novartis Pharmaceuticals);

(14) Topoisomerase inhibitors such as topotecan (Glaxo SmithKline), and Camptosar (Pharmacia);

(15) Vinca alkaloids, such as, navelbine (Anvar and Fabre, France), vincristine and vinblastine;

(16) Antibodies that are inhibitors of alpha V beta 3 integrins, such as, LM-609 (see, Clinical Cancer Research, Vol. 6, page 3056-3061, August 2000, the disclosure of which is incorporated herein by reference thereto); and

(17) Heat Shock Protein HSP90 inhibitors, such as 17-Allylamino-17-demethoxygeldanamycin (17-AAG).

In one embodiment the antineoplastic agents are selected from the group consisting of: paclitaxel, docetaxel, oxaliplatin, carboplatin, cisplatin, gemcitabine, tamoxifen, HERCEPTIN® (Trastuzumab), Cetuximab, TYKERB®, TARCEVA®, IRESSA®, bevacizumab, navelbine, 17-Allylamino-17-demethoxy-geldanamycin, IMC-1C11, SU5416 or SU6688.

In another embodiment the antineoplastic agents are selected from: paclitaxel, docetaxel, carboplatin, cisplatin, navelbine, gemcitabine, 17-Allylamino-17-demethoxygeldanamycin (17-AAG), TYKERB®, or HERCEPTIN® (Trastuzumab).

In general when more than one antineoplastic agent is used in the methods of this invention, the antineoplastic agents are administered on the same day either concurrently or consecutively in their standard dosage form. For example, the antineoplastic agents are usually administered intravenously, preferably by an IV drip using IV solutions well known in the art (e.g., isotonic saline (0.9% NaCl) or dextrose solution (e.g., 5% dextrose).

When two or more antineoplastic agents are used, the antineoplastic agents are generally administered on the same day; however, those skilled in the art will appreciate that the antineoplastic agents can be administered on different days and in different weeks. The skilled clinician can administer the antineoplastic agents according to their recommended dosage schedule from the manufacturer of the agent and can adjust the schedule according to the needs of the patient, e.g., based on the patient's response to the treatment. For example, when gemcitabine is used in combination with a platinum coordinator compound, such as, for example, cisplatin, to treat lung cancer, both the gemcitabine and the cisplatin are given on the same day on day one of the treatment cycle, and then gemcitabine is given alone on day 8 and given alone again on day 15.

Thus, one embodiment of this invention is directed to a method of treating cancer, said treatment comprising administering to a patient in need of such treatment therapeutically effective amounts of one or more (e.g., one) compounds of Formula 1, 2, 3 or 4, a taxane, and a platinum coordination compound.

Another embodiment of this invention is directed to a method of treating cancer comprising administering to a patient in need of such treatment therapeutically effective amounts of one or more (e.g., one) compounds of Formula 1, 2, 3 or 4, a taxane, and a platinum coordination compound, wherein said compound of Formula 1, 2, 3 or 4 is administered every day, said taxane is administered once per week per cycle, and said platinum coordinator compound is administered once per week per cycle. In one embodiment, the treatment is for one to four weeks per cycle.

Another embodiment of this invention is directed to a method of treating cancer comprising administering to a patient in need of such treatment therapeutically effective amounts of one or more (e.g., one) compounds of Formula 1, 2, 3 or 4, a taxane, and a platinum coordination compound, wherein said compound of Formula 1, 2, 3 or 4 is administered every day, said taxane is administered once every three weeks per cycle, and said platinum coordinator compound is administered once every three weeks per cycle. in one embodiment, the treatment is for one to three weeks per cycle.

Another embodiment of this invention is directed to a method of treating cancer, said treatment comprising administering to a patient in need of such treatment therapeutically effective amounts of one or more (e.g., one) compounds of Formula 1, 2, 3 or 4, paclitaxel, and carboplatin. In one embodiment, said kinase inhibitor is administered every day, said paclitaxel is administered once per week per cycle, and said carboplatin is administered once per week per cycle. In another embodiment, the treatment is for one to four weeks per cycle.

Another embodiment of this invention is directed to a method of treating cancer, said treatment comprising administering to a patient in need of such treatment therapeutically effective amounts of one or more (e.g., one) compounds of Formula 1, 2, 3 or 4, paclitaxel, and carboplatin. In one embodiment, said compound of Formula 1, 2, 3 or 4 is administered every day, said paclitaxel is administered once every three weeks per cycle, and said carboplatin is administered once every three weeks per cycle. In another embodiment, the treatment is for one to three weeks per cycle.

Other embodiments of this invention are directed to methods of treating cancer as described in the above embodiments except that in place of paclitaxel and carboplatin the taxanes and platinum coordinator compounds used together in the methods are: (1) docetaxel (Taxotere) and cisplatin; (2) paclitaxel and cisplatin; and (3) docetaxel and carboplatin. In one embodiment of the methods of this invention the cisplatin is used in amounts of about 30 to about 100 mg/m$^2$. In one embodiment of the methods of this invention docetaxel is used in amounts of about 30 to about 100 mg/m$^2$.

In another embodiment this invention is directed to a method of treating cancer, said treatment comprising administering to a patient in need of such treatment therapeutically effective amounts of one or more (e.g., one) compounds of Formula 1, 2, 3 or 4, a taxane, and an EGF inhibitor that is an antibody. In one embodiment the taxane used is paclitaxel, and the EGF inhibitor is a HER2 antibody (e.g., Herceptin) or Cetuximab, and in one embodiment Herceptin is used. The length of treatment, and the amounts and administration of the compounds of Formula 1, 2, 3 or 4 and the taxane are as described in the embodiments above. The EGF inhibitor that is an antibody is administered once a week per cycle, and, in one embodiment, is administered on the same day as the taxane, and in another embodiment is administered consecutively with the taxane. For example, Herceptin is administered in a loading dose of about 3 to about 5 mg/m$^2$ (preferably about 4 mg/m$^2$), and then is administered in a maintenance dose of about 2 mg/m$^2$ once per week per cycle for the remainder of the treatment cycle (usually the cycle is 1 to 4 weeks). In one embodiment, the cancer treated is breast cancer.

In another embodiment this invention is directed to a method of treating cancer, said treatment comprising administering to a patient in need of such treatment therapeutically effective amounts of:

(1) One or more (e.g., one) compounds of Formula 1, 2, 3 or 4;

(2) A taxane; and (3) An antineoplastic agent selected from the group consisting of: (a) An EGF inhibitor that is a small molecule; (b) A VEGF inhibitor that is an antibody; and (c) A VEGF kinase inhibitor that is a small molecule. In one embodiment, the taxane paclitaxel or docetaxel is used. In another embodiment, the antineoplastic agent is selected from: tarceva, Iressa, bevacizumab, SU5416 or SU6688. The length of treatment, and the amounts and administration of the compound of Formula 1, 2, 3 or 4 and the taxane are as described in the embodiments above. The VEGF kinase inhibitor that is an antibody is usually given once per week per cycle. The EGF and VEGF inhibitors that are small molecules are usually given daily per cycle. In one embodiment, the VEGF inhibitor that is an antibody is given on the same day as the taxane, and in another embodiment is administered concurrently with the taxane. When the EGF inhibitor that is a small molecule or the VEGF inhibitor that is a small molecule is administered on the same day as the taxane, the administration, in one embodiment, is concurrently with the taxane. The EGF or VEGF kinase inhibitor is generally administered in an amount of about 10 to about 500 mg/m$^2$.

In another embodiment this invention is directed to a method of treating cancer, said treatment comprising administering to a patient in need of such treatment therapeutically effective amounts of one or more (e.g., one) compounds of Formula 1, 2, 3 or 4, an anti-tumor nucleoside derivative, and a platinum coordination compound.

Another embodiment of this invention is directed to a method of treating cancer, said treatment comprising administering to a patient in need of such treatment therapeutically effective amounts of one or more (e.g., one) compounds of Formula 1, 2, 3 or 4, an anti-tumor nucleoside derivative, and a platinum coordination compound, wherein said compounds of Formula 1, 2, 3 or 4 are administered every day, said anti-tumor nucleoside derivative is administered once per week per cycle, and said platinum coordinator compound is administered once per week per cycle. Although the treatment can be for one to four weeks per cycle, the treatment, in one embodiment, is for one to seven weeks per cycle.

Another embodiment of this invention is directed to a method of treating cancer, said treatment comprising administering to a patient in need of such treatment therapeutically effective amounts of one or more (e.g., one) compounds of Formula 1, 2, 3 or 4, an anti-tumor nucleoside derivative, and a platinum coordination compound, wherein said compounds of Formula 1, 2, 3 or 4 are administered every day, said an anti-tumor nucleoside derivative is administered once per week per cycle, and said platinum coordinator compound is administered once every three weeks per cycle. Although the treatment can be for one to four weeks per cycle, the treatment in one embodiment, is for one to seven weeks per cycle.

Another embodiment of this invention is directed to a method of treating cancer, said treatment comprising administering to a patient in need of such treatment therapeutically effective amounts of one or more (e.g., one) compounds of Formula 1, 2, 3 or 4, gemcitabine, and cisplatin. In one embodiment, said compounds of Formula 1, 2, 3 or 4 are administered every day, said gemcitabine is administered once per week per cycle, and said cisplatin is administered once per week per cycle. In one embodiment, the treatment is for one to seven weeks per cycle.

Another embodiment of this invention is directed to a method of treating cancer, said treatment comprising administering to a patient in need of such treatment therapeutically effective amounts of one or more (e.g., one) compounds of Formula 1, 2, 3 or 4, gemcitabine, and cisplatin. In one embodiment, said compounds of Formula 1, 2, 3 or 4 are administered every day, said gemcitabine is administered once per week per cycle, and said cisplatin is administered once every three weeks per cycle. In one embodiment, the treatment is for one to seven weeks.

Another embodiment of this invention is directed to a method of treating cancer, said treatment comprising administering to a patient in need of such treatment therapeutically effective amounts of one or more (e.g., one) compounds of Formula 1, 2, 3 or 4), gemcitabine, and carboplatin. In one embodiment, said compounds of Formula 1, 2, 3 or 4 are administered every day, said gemcitabine is administered once per week per cycle, and said carboplatin is administered once per week per cycle. In another embodiment, the treatment is for one to seven weeks per cycle.

Another embodiment of this invention is directed to a method of treating cancer, said treatment comprising administering to a patient in need of such treatment therapeutically effective amounts of one or more (e.g., one) compounds of Formula 1, 2, 3 or 4, gemcitabine, and carboplatin. In one embodiment, said compounds of Formula 1, 2, 3 or 4 are administered every day, said gemcitabine is administered once per week per cycle, and said carboplatin is administered once every three weeks per cycle. In one embodiment, the treatment is for one to seven weeks per cycle.

In the above embodiments using gemcitabine, the compounds of Formula 1, 2, 3 or 4 and the platinum coordinator compound are administered as described above for the embodiments using taxanes. Gemcitabine is administered in an amount of about 500 to about 1250 mg/m$^2$. The gemcitabine, in one embodiment, is administered on the same day as the platinum coordinator compound, and in another embodiment consecutively with the platinum coordinator compound, and in another embodiment gemcitabine is administered after the platinum coordinator compound.

Another embodiment of this invention is directed to a method of treating cancer in a patient in need of such treatment comprising administering to said patient one or more (e.g., one) compounds of Formula 1, 2, 3 or 4 and an antineoplastic agent selected from: (1) EGF inhibitors that are antibodies, (2) EGF inhibitors that are small molecules, (3) VEGF inhibitors that are antibodies, and (4) VEGF kinase inhibitors that are small molecules all as described above. The treatment is for one to seven weeks per cycle, and generally for one to four weeks per cycle. The compounds of Formula 1, 2, 3 or 4 are administered in the same manner as described above for the other embodiments of this invention. The small molecule antineoplastic agents are usually administered daily, and the antibody antineoplastic agents are usually administered once per week per cycle. The antineoplastic agents, in one embodiment, are selected from: HERCEPTIN® (Trastuzumab), Cetuximab, TARCEVA®, IRESSA®, bevacizumab, IMC-1C11, SU5416 or SU6688.

Other embodiments of this invention are directed to pharmaceutical compositions comprising a compound of Formula 1, 2, 3 or 4, and at least one antihormonal agent and a pharmaceutically acceptable carrier.

Other embodiments of this invention are directed to pharmaceutical compositions comprising a compound of Formula 1, 2, 3 or 4, at least one antihormonal agent, at least one chemotherapeutic agent, and a pharmaceutically acceptable carrier.

Other embodiments of this invention are directed to pharmaceutical compositions comprising a compound of Formula 1, 2, 3 or 4, at least one chemotherapeutic agent, and a pharmaceutically acceptable carrier.

Those skilled in the art will recognize that the actual dosages and protocols for administration employed in the methods of this invention may be varied according to the judgement of the skilled clinician. A determination to vary the dosages and protocols for administration may be made after the skilled clinician takes into account such factors as the patient's age, condition and size, as well as the severity of the cancer being treated and the response of the patient to the treatment.

The particular choice of antihormonal agents, optional chemotherapeutic agents and optional radiation will depend upon the diagnosis of the attending physicians and their judgment of the condition of the patient and the appropriate treatment protocol.

The determination of the order of administration, and the number of repetitions of administration of the antihormonal agents, optional chemotherapeutic agents and optional radiation during a treatment protocol, is well within the knowledge of the skilled physician after evaluation of the breast cancer being treated and the condition of the patient.

Thus, in accordance with experience and knowledge, the practicing physician can modify each protocol for the administration of antihormonal agents, optional chemotherapeutic agents and optional radiation according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

In the embodiments of this invention wherein a platinum coordinator compound is used as well as at least one other antineoplastic agent, and these drugs are administered consecutively, the platinum coordinator compound is generally administered after the other antineoplastic agents have been administered.

Other embodiments of this invention include the administration of a therapeutically effective amount of radiation to the patient in addition to the administration of the compounds of Formula 1, 2, 3 or 4 and antineoplastic agents in the embodiments described above. Radiation is administered according to techniques and protocols well know to those skilled in the art.

Another embodiment of this invention is directed to a pharmaceutical composition comprising at least two different antineoplastic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising at least one compound of Formula 1, 2, 3 or 4 (usually one) and at least two different antineoplastic agents and a pharmaceutically acceptable carrier for intravenous administration. In one embodiment, the pharmaceutically acceptable carrier is an isotonic saline solution (0.9% NaCl), preferably containing solubilizing agents such as polyethylene glycols or polyvinyl pyrrolidones, or a dextrose solution (e.g., 5% dextrose).

Another embodiment of this invention is directed to a pharmaceutical composition comprising at least one compound of Formula 1, 2, 3 or 4 (usually one) and at least one antineoplastic agent and a pharmaceutically acceptable carrier for intravenous administration. In one embodiment, the pharmaceutically acceptable carrier is an isotonic saline solution (0.9% NaCl), preferably containing solubilizing agents such as polyethylene glycols or polyvinyl pyrrolidones, or a dextrose solution (e.g., 5% dextrose).

Those skilled in the art will appreciate that the compounds (drugs) used in the methods of this invention are available to the skilled clinician in pharmaceutical compositions (dosage forms) from the manufacturer and are used in those compositions. So, the recitation of the compound or class of compounds in the above described methods can be replaced with a recitation of a pharmaceutical composition comprising the particular compound or class of compounds. For example, the embodiment directed to a method of treating cancer comprising administering to a patient in need of such treatment therapeutically effective amounts of the compounds of Formula 1, 2, 3 or 4, a taxane, and a platinum coordination compound, includes within its scope a method of treating cancer comprising administering to a patient in need of such treatment therapeutically effective amounts of a pharmaceutical composition comprising at least one compound of Formula 1, 2, 3 or 4 (usually one), a pharmaceutical composition comprising a taxane, and a pharmaceutical composition comprising a platinum coordination compound.

The actual dosage employed may be varied depending upon the requirements of the patient and the severity of the condition being treated. Determination of the proper dosage for a particular situation is within the skill of the art.

The amount and frequency of administration of the compounds of Formula 1, 2, 3 or 4 and the antineoplastic agents will be regulated according to the judgment of the attending clinician (physician) considering such factors as age, condition and size of the patient as well as severity of the cancer being treated.

The antineoplastic agent can be administered according to therapeutic protocols well known in the art. It will be apparent to those skilled in the art that the administration of the antineoplastic agent can be varied depending on the cancer being treated and the known effects of the antineoplastic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of antineoplastic agent will depend upon the diagnosis of the attending physicians and their judgement of the condition of the patient and the appropriate treatment protocol.

The determination of the order of administration, and the number of repetitions of administration of the antineoplastic agent during a treatment protocol, is well within the knowledge of the skilled physician after evaluation of the cancer being treated and the condition of the patient.

Thus, in accordance with experience and knowledge, the practicing physician can modify each protocol for the administration of an antineoplastic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain, cough (for lung cancer), and shortness of breath (for lung cancer)), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Chemotherapeutic Agents

Classes of compounds that can be used as chemotherapeutic agents (antineoplastic agent/microtubule affecting agents in combination with a compound of the invention include, but are not limited to: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol and is described in more detail below in the subsection entitled "Microtubule Affecting Agents"), paclitaxel derivatives (e.g. taxotere), Mithramycin, Deoxyco-formycin, Mitomycin-C, L-Asparaginase, Interferons (especially IFN-a), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Other chemotherapeutics include Navelbene, CPT-11, Anastrazole, Letrazole, Capecitabinbe, Reloxafine, and Droloxafine.

Particularly preferred are the antineoplastic agents selected from Cyclophasphamide, 5-Fluorouracil, Temozolomide, Vincristine, Oxaliplatin, Cisplatin, Carboplatin, 17-Allylamino-17-demethoxygeldanamycin (17-AAG), and Gemcitabine. Most preferably, the antineoplastic agent is selected from Gemcitabine, Cisplatin and Carboplatin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), 57th Edition (Thomson PDR, Montvale, N.J. 07645-1742); the disclosure of which is incorporated herein by reference thereto.

Microtubule Affecting Agents

As used herein, a microtubule affecting agent (e.g., paclitaxel, a paclitaxel derivative or a paclitaxel-like compound) that can be used in combination with a compound of the invention is a compound that interferes with cellular mitosis, i.e., having an anti-mitotic effect, by affecting microtubule formation and/or action. Such agents can be, for instance, microtubule stabilizing agents or agents that disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol, NSC 125973), paclitaxel derivatives (e.g., Taxotere, NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) Science, 274:2009) estramustine, nocodazole, MAP4, and the like. Examples of such agents are also described in the scientific and patent literature, see, e.g., Bulinski (1997) J. Cell Sci. 110:3055-3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem. 271:29807-29812.

Particularly preferred agents are compounds with paclitaxel-like activity. These include, but are not limited to paclitaxel and paclitaxel derivatives (paclitaxel-like compounds) and analogues. Paclitaxel and its derivatives (e.g. Taxol and Taxotere) are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol (NSC number: 125973). Taxol inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17-23, Horwitz (1992) Trends Pharmacol. Sci. 13: 134-146, Rowinsky (1990) J. Natl. Canc. Inst. 82: 1247-1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37-47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

Compounds with possible tubulin polymerization activity can be screened in vitro. For example, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) Lab. Anim. Sci., 45(2):145-150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) J. Molec. Biol., 89: 737-758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition, their administration is described in the standard literature. For example, the administration of many of the chemotherapeutic agents is described in the "Physicians' Desk Reference" (cited above).

Kits

Advantageously, the present invention also provides kits for use by a consumer for treating disease. The kits comprise a) a pharmaceutical composition comprising a compound of the invention (e.g., a compound of the Formula 1, 2, 3, or 4) and a pharmaceutically acceptable carrier, vehicle or diluent; and, optionally, b) instructions describing a method of using the pharmaceutical composition for treating the specific disease.

A "kit" as used in the instant application includes a container for containing the separate unit dosage forms such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It maybe desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," ... etc. ... "Second Week, Monday, Tuesday, ..." etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter, which indicates the number of daily doses that, has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Superior Potency and Kinase Selectivity of Compounds 1-4

Compounds 1-4 are the most potent and efficacious compounds within the scope structures of the general formula 5:

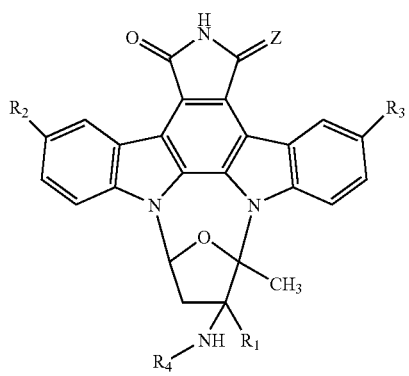

Substituents $R_2$ and $R_3$ other than H generally cause a correlated decrease in potency for inhibition of cell cycle associated kinases and tumor proliferation. Substituents in $R_4$ other than H, as exemplified in WO97/05140, abolish activity against cell cycle control kinases completely. Table 1 shows that kinase inhibitory potency of the preferred compound 6 of WO97/05140 (general formula 5 with $R_1$=COOCH$_3$, $R_2$, $R_3$, $R_4$=H, Z=H,H) is improved at least by an order of magnitude by 1 with the substituent $R_1$=CONHR$_6$ ($R_6$=H or CH$_3$, other substituents $R_6$ significantly reduce or abolish activity). This decisive impact of specifically $R_1$=CONHCH$_3$ or CONH$_2$, imparting a similar potency and selectivity to 2-3 compared to 1, was not recognized in patent application WO97/05140. Moreover, the effect of the combination of the preferred $R_1$ substituents with the specific amino group —NHR($R_4$=H) in imparting extraordinary anti-proliferative potency, while allowing for very fortuitous pharmaceutical properties related to safety and convenience of dosing, has not been demonstrated.

Relative to the compounds disclosed in WO00/01699 and WO04/048384, compounds of the structural formula 1-4 have a higher degree of selectivity in favor of several antiproliferative kinases, as exemplified for the representative compound 1 and directly related compounds 7 of WO04/048384 and 8-9 of WO00/01699, containing the general scaffold of 10, respectively. As the selectivity profile proved to be rather invariant to the substitution pattern in 10, lack of selectivity is clearly a property of the scaffold 10. Table 2 shows the differentiation of the target kinases versus GSK3 and the second messenger kinases PKC and PKA under identical kinase assay conditions by 1, but not 7-9. Compounds 2, 3 and 4 have a virtually identical potency and selectivity profile as 1, indicating that the group Z (H, H or O) and the substitution of —CH$_3$ by H in R$_6$ of scaffold 5 has little impact on these parameters.

Together with their improved solubility, especially in their salt form, compounds 1-4 represent substantially improved therapeutic agents for indications where kinases involved in proliferation control are dysregulated.

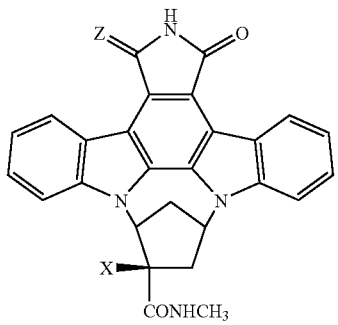

10

| | X | Z |
|---|---|---|
| 7 | —NH$_2$ | H, H |
| 8 | —OH | =O |
| 9 | —OH | H, H |

Superior Antiproliferative Activity of 1 over the Compound 6

The anti-tumor activity of compounds of the formula 1-4 was assessed in several tumor cell lines relative to the known compound 6, which exhibits the highest kinase inhibitory potency among the exemplified compounds of the disclosure WO97/05140. Of particular interest for future innovation in the cancer area are such cell lines where the transformed status is maintained independently of constitutive receptor activation. For example, estrogen receptor activation is frequent in breast cancer, and the efficacies of therapies based on Tamoxifen and similar compounds depend on this oncogenic mechanism. Also, mutations of the epidermal growth factor (EGF) receptor (HER or ERB receptors) is a frequent feature in breast cancer and glioblastomas, and thus targeted by the respective tyrosine kinase domain inhibitors, like Iressa or Tykerb, or by monoclonal antibodies like Herceptin. The common clinical experience with all these approaches is efficacy in a subpopulation of patients only, where significant initial tumor responses are recorded, but even then improvement of survival times in responders is limited. These limitations are probably related to the heterogeneity of oncogenic mechanisms in an established tumor. Initial responses are only observed if the targeted molecular mechanism happens to be dominant in the tumor. However, even if this is the case, oncogenic mechanisms represented in the minor tumor cell population eventually become selected under therapy, and a recurrent tumor with a molecular mechanism or combinations thereof different from the original tumor becomes established, limiting longer term survival prospects. This situation was high-lighted in a survey of a broad panel of breast cancer cell lines, showing that even the relatively frequent constitutive activation of ERBs (EGF receptors) comprised only about 20% of the panel [Konecny et al., Cancer Res. 66, 1630-1639 (2006)]. Coincidentally, responder rates to Herceptin are not much different at about 30%.

For the purpose of demonstrating the improvement over known compounds and the broader applicability of the compounds of the present invention, and their utility in cases where the current more targeted therapies discussed above fail, human cell lines with disparate oncogenic mechanisms were selected, represented but not limited by:

1) the highly metastasizing and invasive MDA-MB-231 breast cancer cell line, which is both estrogen and EGF-receptor independent and is one of the most unresponsive cell lines to Tykerb. Additionally, it harbors both a raf- as well as a ras-mutation, which makes it insensitive to specific inhibition of the MAP-kinase pathway;
2) the EGF-receptor independent glioblastoma cell line U373, mainly driven by the loss of tumor suppressor activities of PTEN (Phosphatase/tensin homolog, PI3K pathway) and p53;
3) the colon carcinoma cell line HT29, generally regarded as one of the most challenging tumor cells in mouse xenograft models.

FIG. 1 shows that a concentration of 10 nM of the compound of the formula 1 almost completely prevents the growth of MDA-MB-231 cells over 1 week of exposure, while the known compound 6 was virtually ineffective at that concentration under directly comparable conditions, and required a ten-fold higher concentration to exhibit a similar effect.

Figure 2:
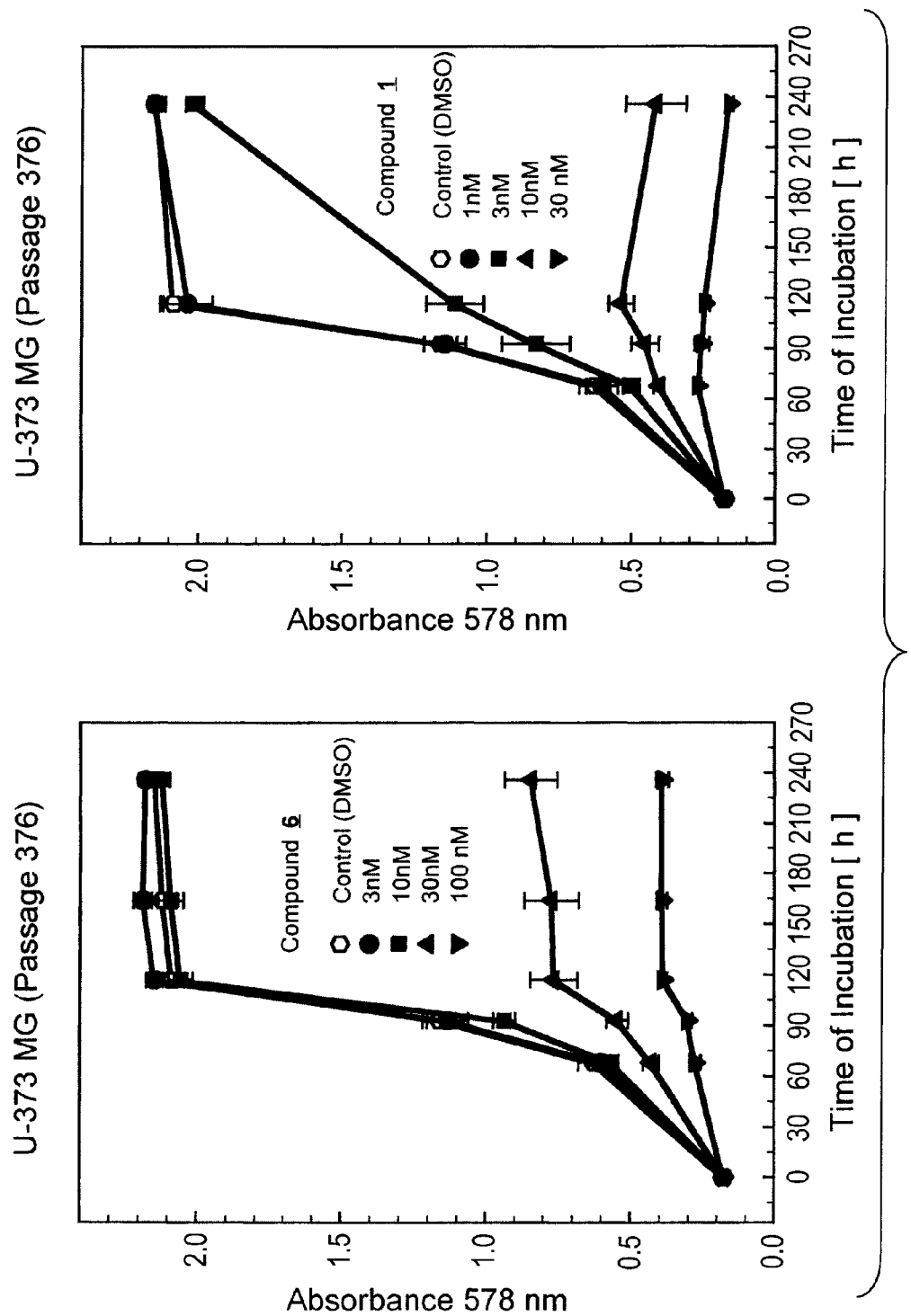
FIG. 2 shows growth curves for the U373 glioblastoma cell line (Example 5) at increasing concentrations of compound 1, compared to the less potent known compound 6.

FIG. 2 shows that the compound of the formula 1 was almost completely effective at 10 nM in arresting the growth of U373 cells over a week, while compound 6 required once more a ten-fold higher concentration to reach a similar effect.

10 nM of the compound of the formula 1 was also sufficient to block the proliferation of HT29 cells, while compound 6 was completely ineffective at that concentration. In addition, the behavior of the compound of the formula 1 was much more dose-dependent in this case.

Of particular interest is the ability of the compounds of the present invention, especially 1, to induce sustained inhibition over at least one week after a single exposure for a short period between 1 and 6 hrs to a therapeutically relevant concentration of 100 nM (FIG. 4a-c). This feature can be exploited to substantially increase the therapeutic safety margin and pharmacoeconomics of the treatment regimen, in that patients suffering from cancer would already benefit from intermittent exposure to the compounds of the formula 1-4.

Compounds of the formula 1-4 belong to the most potent anti-tumor agents known to date. FIG. 5 shows that the example compound of the formula 1 matches the activity of vinblastine, without having its acute toxicity and limitations to intra-venous application, and is substantially more potent and efficacious than the established general anti-tumor agent cis-platin. The activity of the compound of the formula 1 also compares favorably to the widely used agent Taxol.

An important concern for all anti-tumor agents are limitations of efficacy arising from susceptibility to exclusion from cell entry by multi-drug resistant protein (MDR) and similar drug efflux transporters (ABC cassette proteins). FIG. 6 shows that the anti-proliferative potency range of the compound of the formula 1 (as defined in FIG. 1-3), is more clearly separated than the known compound of the formula 6 from the uptake concentration for the two most frequently involved drug efflux transporters (MDR proteins) ABC-G2 (gp170) and ABC-B1 (BCRP). Development of resistance to treatment by expressing MDR proteins in tumor cell populations is therefore not to be expected for the compounds of the present invention. This advantage is mainly owed to the higher potency of compounds of the present invention, which is therefore critical to clinical utility.

The solubility in aqueous environments for compounds represented by 1-4 and 6 is generally limited to about 1 µM, and sustained plasma levels over 1 µM are not reachable with practicable forms of dosing. With the plasma binding at effective concentrations in both rodents and humans determined at about 80%, the maximal free concentrations sustained over prolonged periods of time are about 200 nM. At these concentrations compounds with the potency of compound 6 are not significantly efficacious in vivo.

Figure 7A:
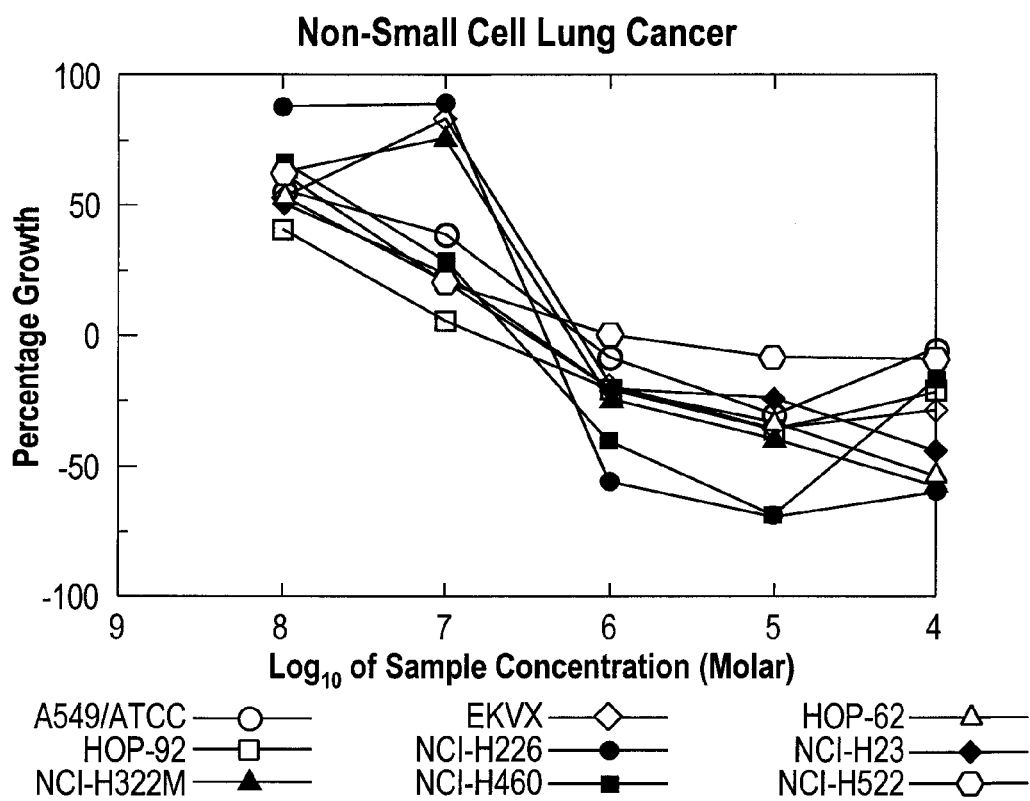
FIGS. 7*a-h* show the inhibitory potencies of compound 1 in the cell lines of the NCI panel from various cancers. The growth of cells treated with various concentrations of compound 1 was expressed in reference to untreated controls (100%) after 48 hr exposure. Negative growth values represent cell death. Actual concentrations of compound 1 are about two times lower than nominal due to well binding in the 96-well plate format.
Figure 7B:
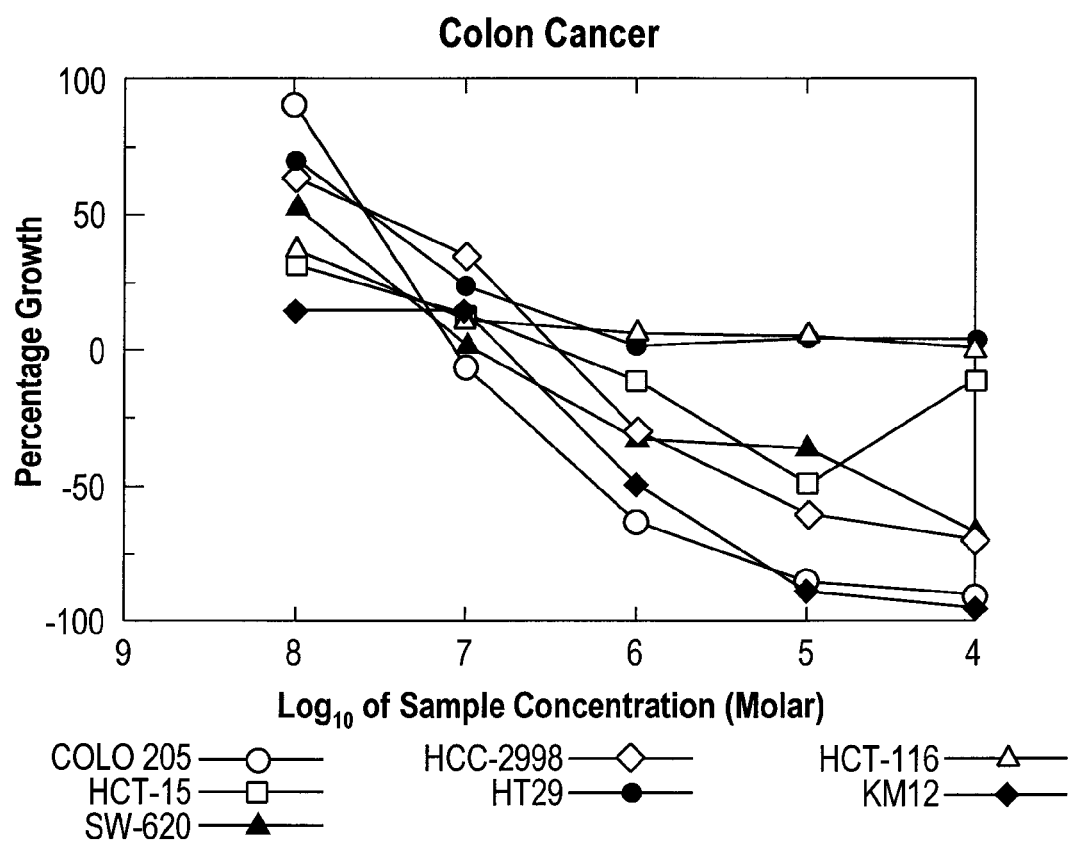
Figure 7C:
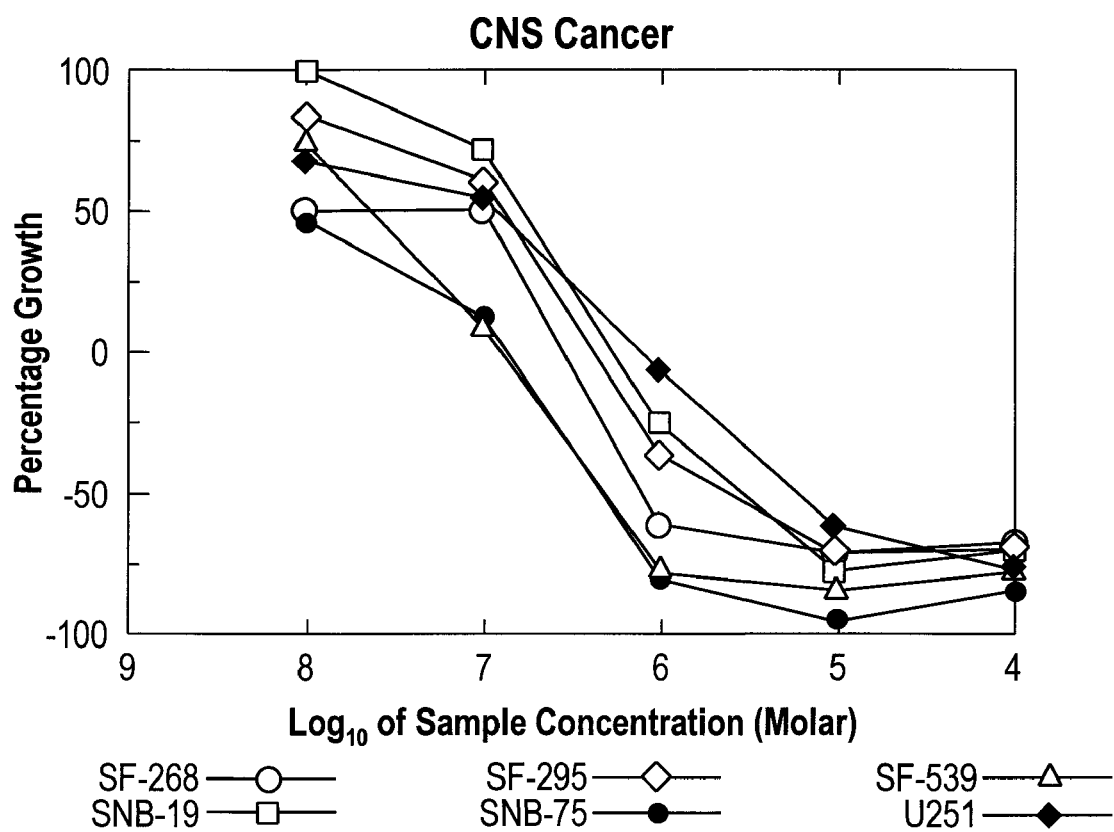
Figure 7D:
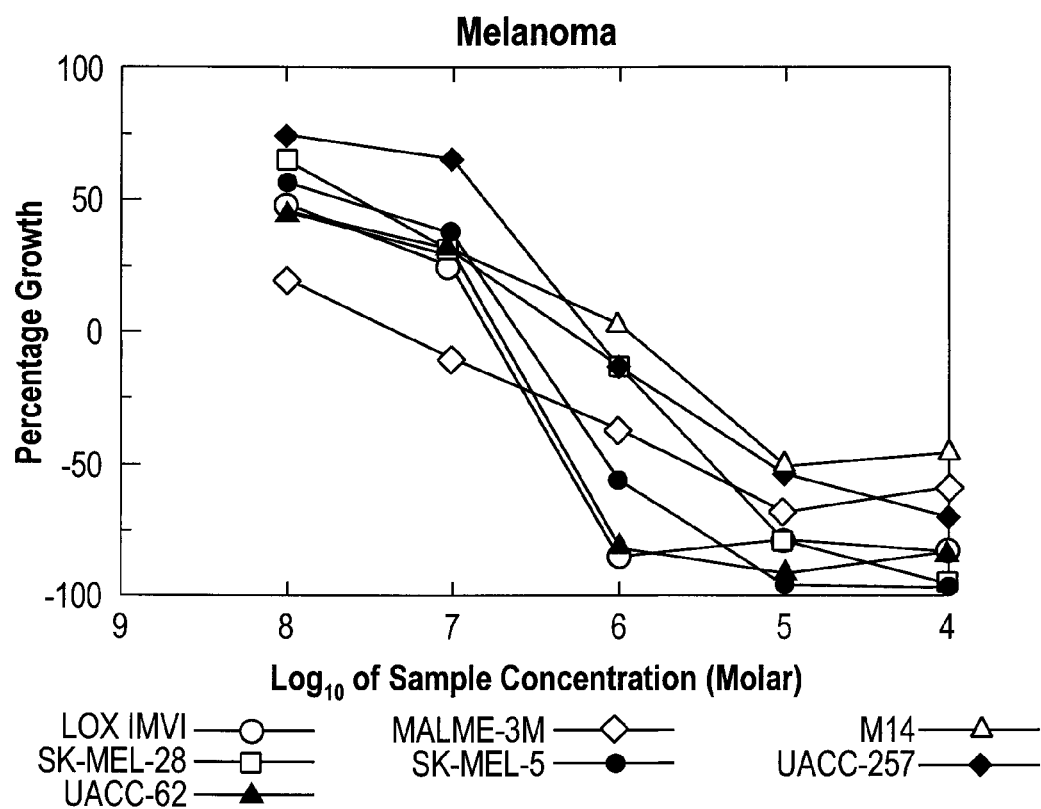
Figure 7E:
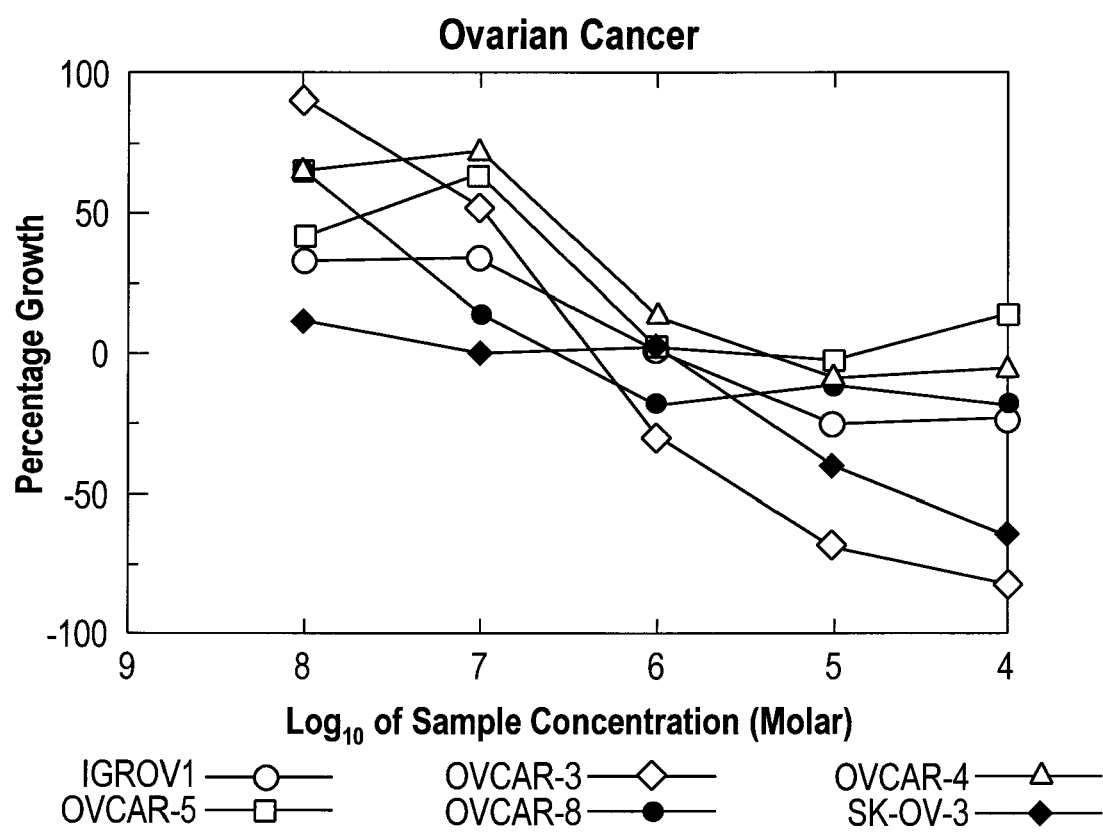
Figure 7F:
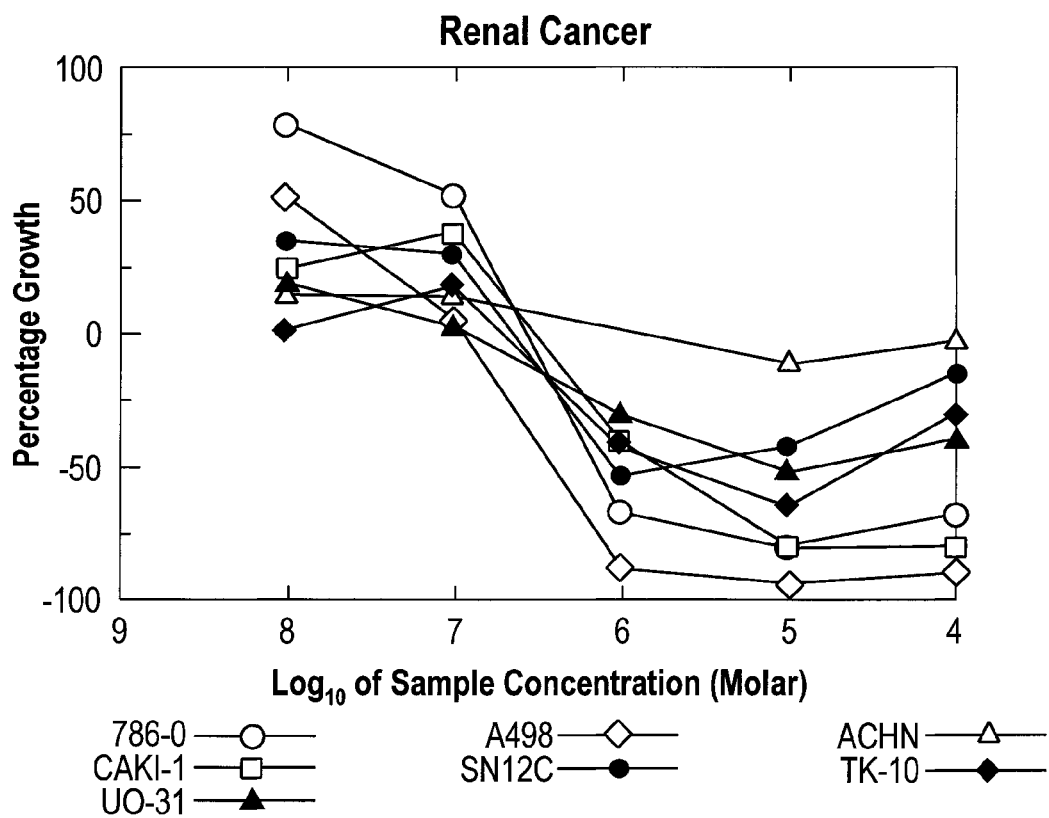
Figure 7G:
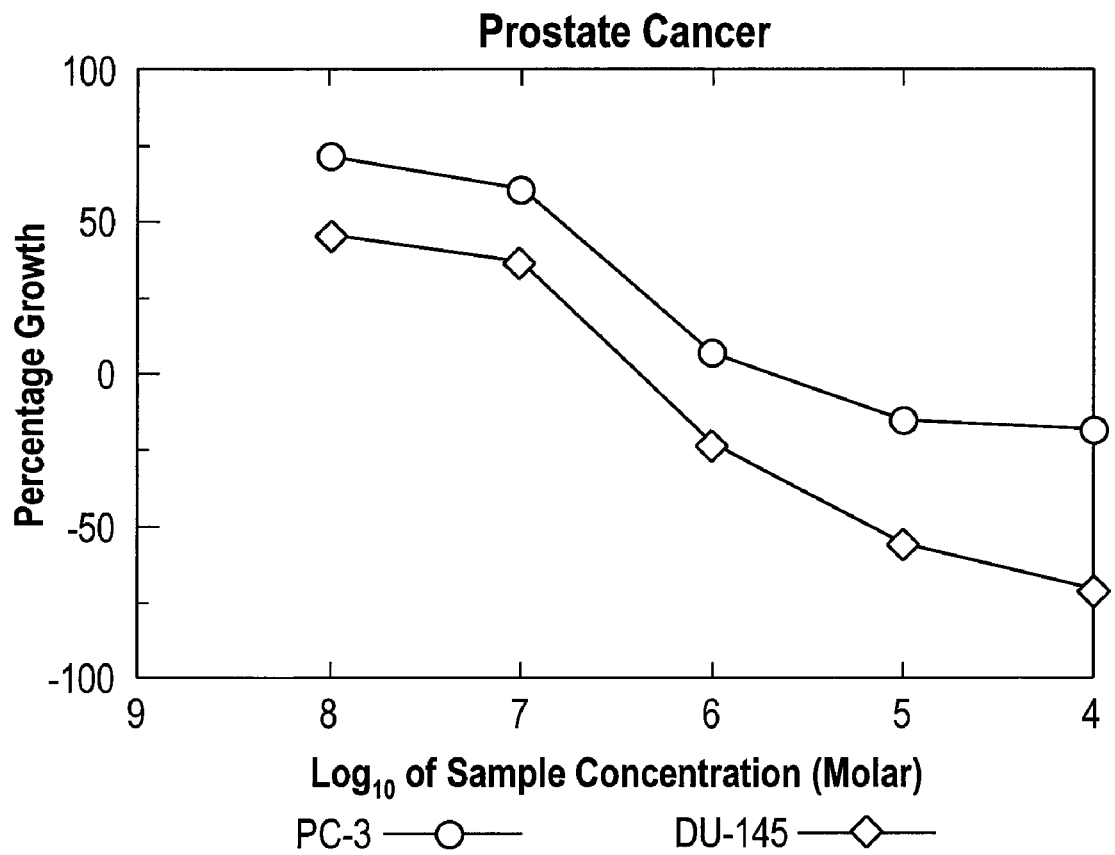
Figure 7H:
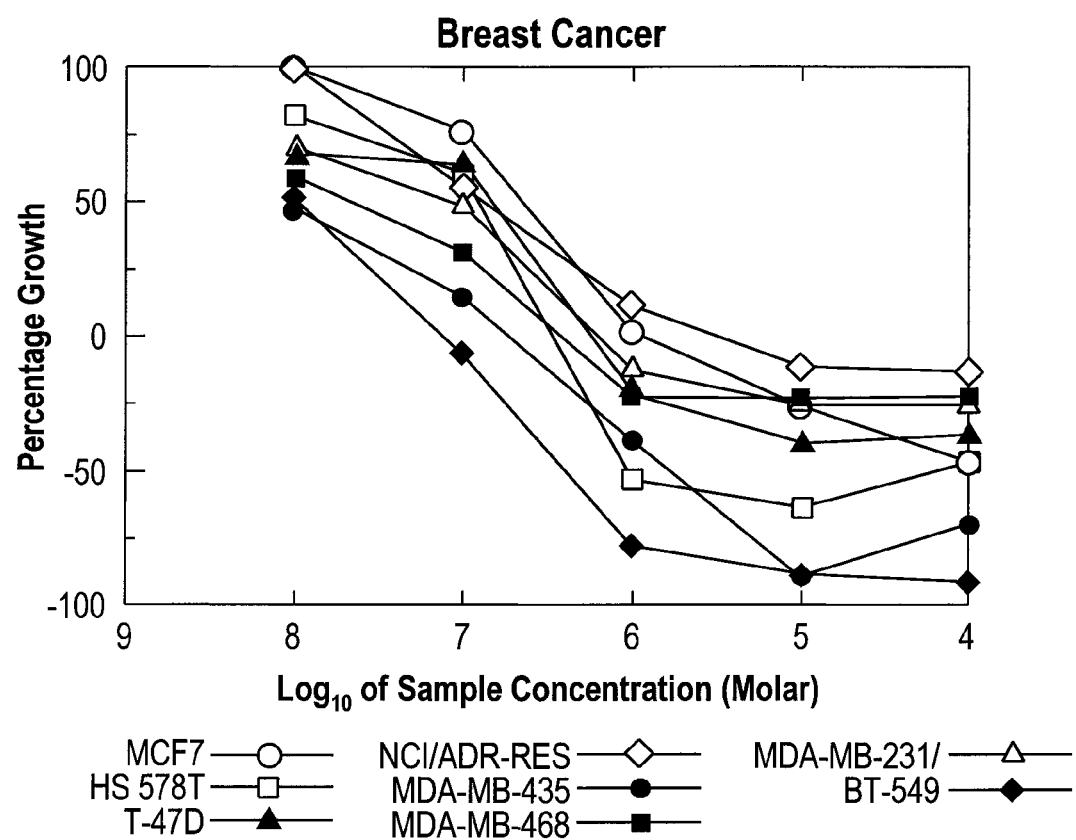
Figure 8:
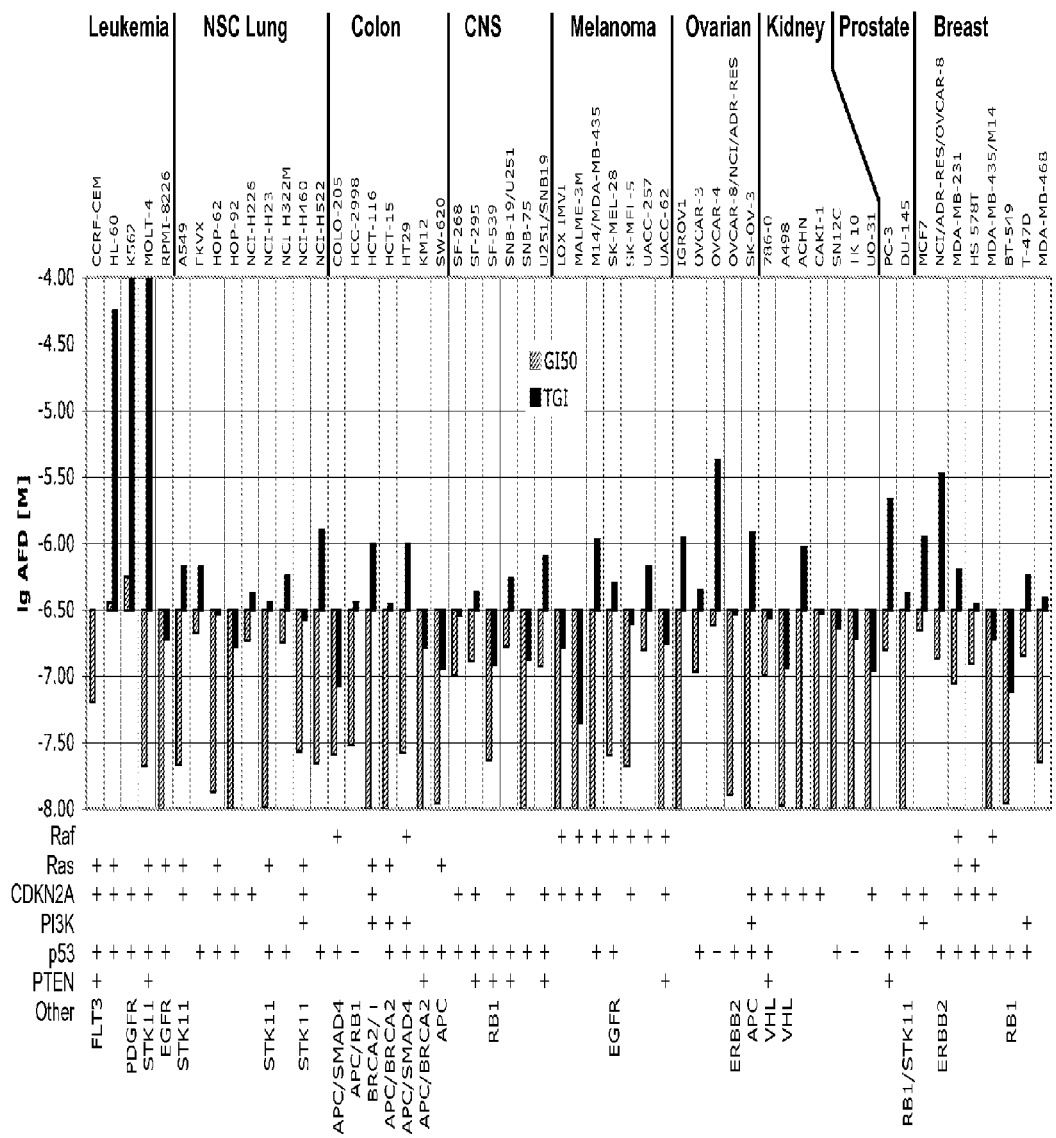
FIG. 8 represents the $GI_{50}$ (50% growth inhibition, crosshatch bars) and TGI (total growth inhibition, solid bars) values of all cells in the NCI-60 panel in relation to the attainable free mouse plasma concentration of orally applied compound 1, corrected for the reduction in actual inhibitor concentration by well binding. The oncogenic mutation spectrum of the cell lines is presented at the bottom.

To further exemplify the breadth of anti-tumor activity of compounds 1-4 the NCI-60 panel was screened with compound 1. The spectrum of verified oncogenic driver mutations in these cell lines was recently elucidated to encompass mutations in raf, ras, CDKN2A (cdk inhibitor), p53, PI3K, PTEN, EGFR, APC, FLT3, RB1 among others. Cell lines generally have several of these mutations representative of stage III and IV cancers [Ikediobi et al., *Mol. Cancer. Ther.* 5, 2606-2612 (2006)]. Significant anti-proliferative activity was seen in all cell lines from lung, colon, brain, skin, ovarian, kidney, prostate, and breast cancers (FIG. 7*a-h*). The average 50% growth inhibition ($GI_{50}$) across all cell lines was at a nominal concentration of 32 nM, with a potency range from <10 nM to 150 nM. Since compound 1 exhibited significant absorption to plastic wells over the 48 hr test time frame, these results underestimate potencies by a factor of about 2. The average concentration for total growth inhibition (TGI) was thus at 200 nM, i.e. about 10-times $GI_{50}$. At sustained free plasma concentrations in vivo of about 200 nM, that can be achieved with practical forms of oral dosing and in the absence of special formulations, all cell lines would be inhibited by more than 50% without exception, and more than half would show no growth at all or would be killed (FIG. 8). These results underscore the broad anti-tumor utility of compounds 1-4, independent of the precise mechanism of oncogenic transformation, or the tissue origin of the tumor.

Treatment of Tumors in Mouse Models by Compounds 1-4

The efficacy of the compound of the formula 1 was confirmed in mouse tumor xenograft models, employing the NMRI(nu/nu) strain of mice. For example, cells from the human tumor cell lines MDA-MB-231, U373, and HT29 were pre-incubated subcutaneously in several nude mice to select for the most robustly growing cell population. After having grown to a sufficient size after 2-3 weeks, a piece of about 2 mm³ volume of the most suitable tumor was transplanted subcutaneously into the region of the thoracic mammary fat pads, an area ensuring a high degree of vascularization of the grafted tissue. When tumors reached a diameter of about 3 mm mice were assigned to treatment groups with about equal average tumor sizes, and therapy was started. Application of the compound of the formula 1 was performed preferably by oral gavage twice daily for continuous exposure, with doses between 1 and 10 mg/kg of the compound of the formula 1 as a solid suspension in water, or in aqueous liquid formulations containing common adjuvants, like polyethylene glycols (PEG), preferentially in form of a salt with a physiologically applicable acid, including but not limited to hydrochloric acid, phosphoric acid, lactic acid, malonic acid, citric acid, etc. Other suitable adjuvants include but are not limited to polyvinyl pyrrolidone (Povidone) of varying average molecular weights. During the course of the treatment, the weight of the animals and the size of the transplanted tumor was monitored three times a week. For maximum efficacy, a daily treatment regimen was chosen at the maximally applicable dose, as defined by the absence of significant weight loss over the course of the treatment. These doses are best determined separately for each individual mouse strain employed.

Figure 9:
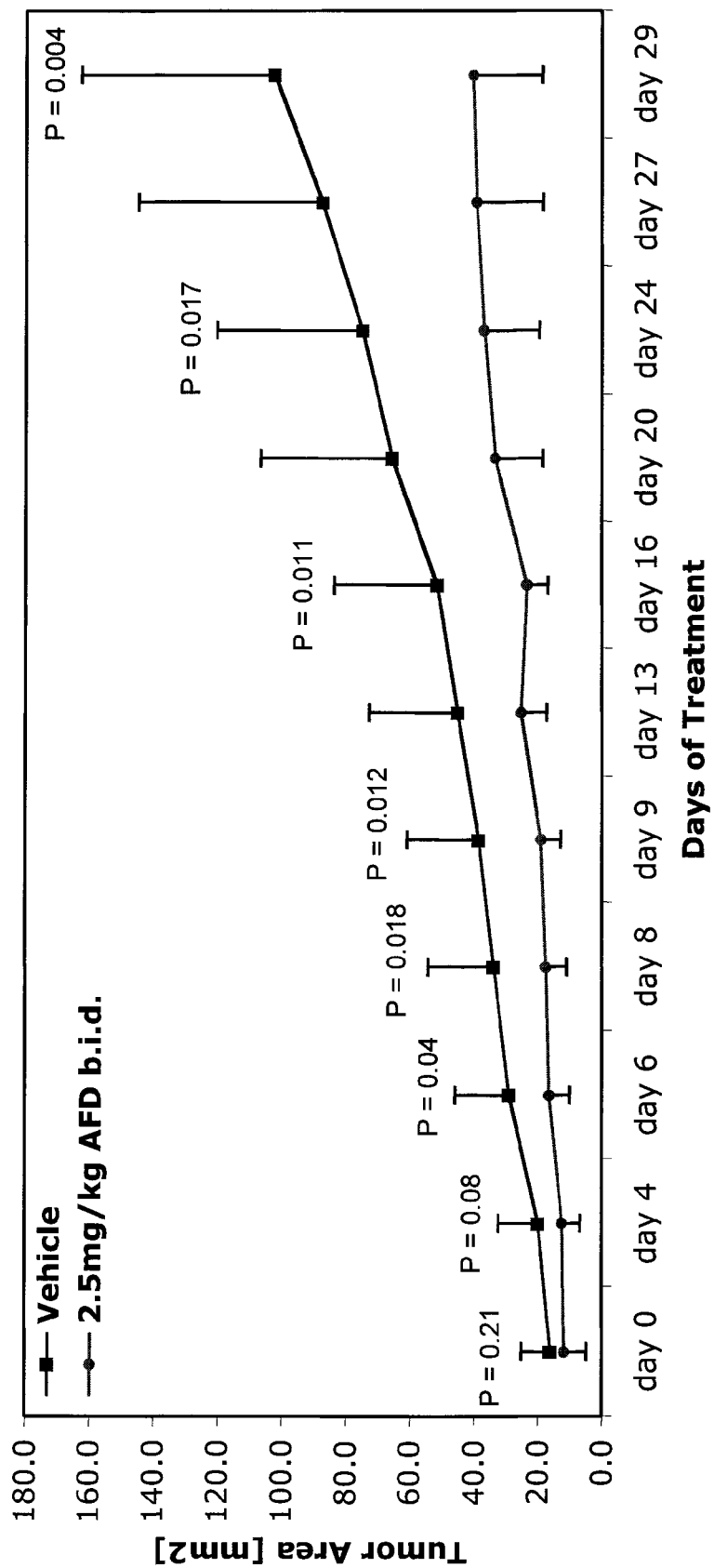
FIG. 9 shows the graphical result of the twice daily 2.5 mg/kg dosing p.o. over 30 days in the HT29 mouse xenograft model described in example 8.
Figure 10:
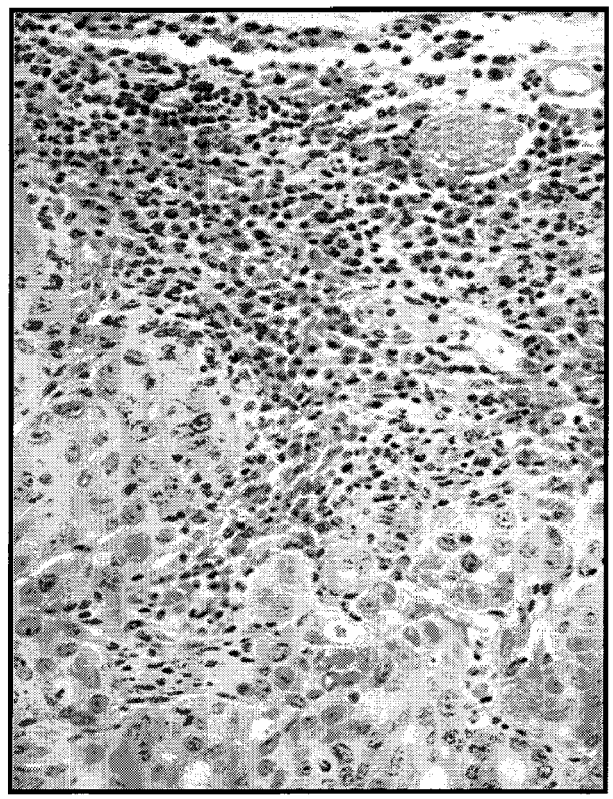
FIG. 10 demonstrates the massive monocyte infiltration seen in tumors of treated mice (B) in example 8, but not in the vehicle control mice (A).

The anti-tumor efficacy of the preferred compound 1 observed in representative xenograft models generally matched the respective in vitro activity in the NCI-60 panel. E.g., twice daily continuous oral dosing regimen of 2.5 mg/kg for 30 days inhibited the growth of a HT29 xenograft by 70% with 2 out of 10 animals showing complete stasis (FIG. 9). The HT29 cell line represents a worst case scenario, since it is the most resistant among the colon cancer derived lines, and is one of the rare tumor cells that cannot be killed by compound 1 even at the highest exposures in vitro (FIG. 7*b*). Besides showing robust anti-proliferative efficacy, tumor histology after 30 days of treatment revealed another important result of treatment with the compound 1: unlike the untreated tumors, the treated tumors all showed massive infiltration by monocytes, probably macrophages (FIG. 10), suggesting a desirable engagement of components of the immune system in clearance activity. This indicates that treatment with the compound 1 did not abrogate important immune functions, which is often counterproductive in standard chemotherapy regimen. Good to excellent efficacy was also noted with a larger panel of xenograft models dosed similarly. Table 3 summarizes the pertinent results with representative xenografts comprising tumors of 8 different organs and diverse combinations of oncogenic driver mutations.

Comparable efficacy as with the example compound of the formula 1 is also obtained with the derivatives of the formulas 2-4. One skilled in the art would understand that similar results can be obtained by alternative application routes, including, but not limited to, intraperitoneal, intravenous, parenteral, transdermal forms of delivery.

Figure 11:
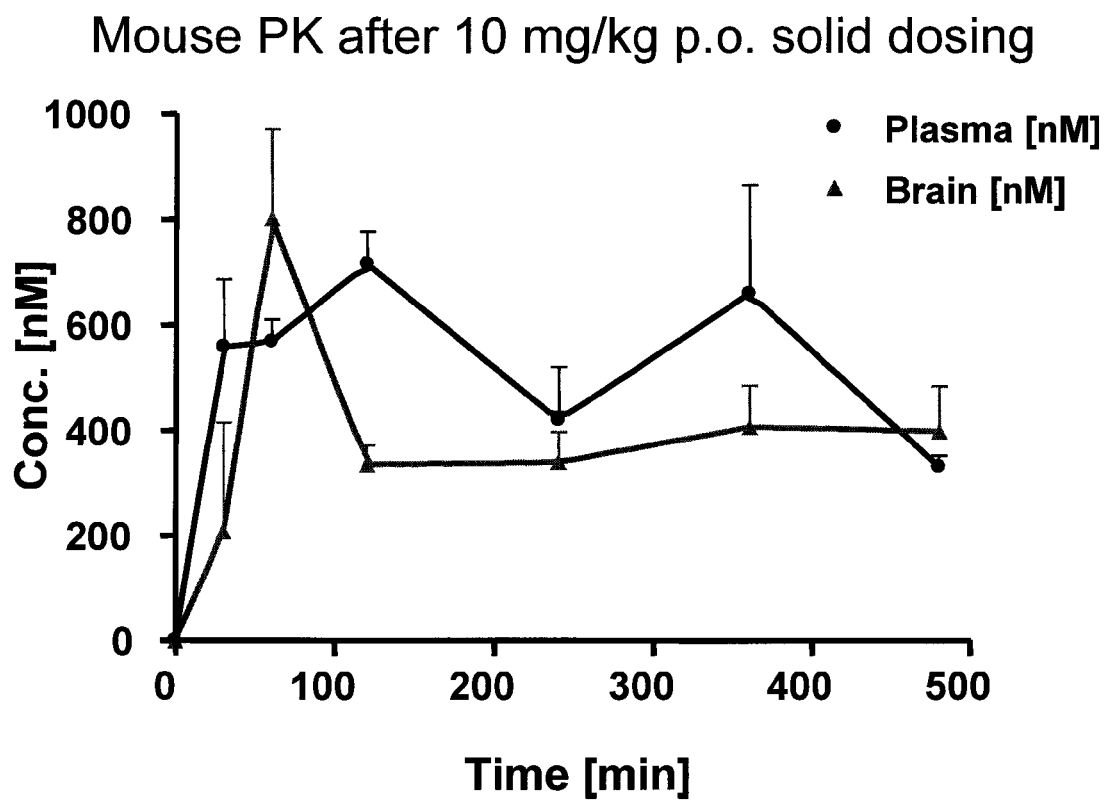
FIG. 11 shows the pharmacokinetic behavior of compound 1 after a single oral dosing of a solid suspension of 10 mg/kg in water, assessed in mouse plasma and brain by the methods described in example 6.

To test for appropriate distribution of the compound of formula 1 into the organs the cell lines employed originated from, orthotopic graft models were employed as well. To this end tumor tissue from human cell lines was implanted after subcutaneous preincubation as above into the organs where the cell line was originally derived from. Thus MDA-MB-231 derived tumors were implanted into mammary glands, HT-29 derived tumors into the colon, and U373 derived tumors into the brain intracranially. The response to treatment was assessed by measuring the tumor sizes relative to vehicle controls after 4 weeks. The efficacy of treatment with compounds of the formula 1-4 was not substantially different in these models than in the subcutaneous graft models, indicating that compounds 1-4 are generally well distributed, including across the blood-brain barrier. The feature of good penetration of the CNS, as illustrated in FIG. 11, in combination with extraordinary anti-proliferative potency is a distinguished feature of the compounds of formula 1-4, but especially of compound 1. The compounds of the present invention are therefore especially useful in treating brain tumors, including but not limited to glioblastomas, astrocytomas, neuroblastomas.

The efficacy of compounds of the formula 1-4 is not limited to graft models of cell lines chosen for convenience and resilience to established therapeutic approaches, but extends to a majority of tumors, as had been indicated by the performance of compound 1 in the NCI-60 panel. The specific compounds of the present invention are broadly active at low dosages by virtue of their potency, selectivity profile, even tissue distribution, including the CNS, and conveniently delivered orally with good bioavailability. Compounds of the formula 1-4, an particularly compounds 1 and 2, do not suffer from the extreme human serum binding of related compounds PKC-412 and UCN-01 [Propper et al., J. Clin. Oncol. 19, 1485-1492 (2001)] used for the treatment of cancer, thus enabling their use in low dosage forms and increasing safe use by reasonably rapid clearance in the event of side effects.

A decisive advantage of compounds of the formula 1-4 is the inherent safety provided by the solubility limit at about 1 µM in aqueous environments. While just about sufficiently high to allow for near complete anti-proliferative efficacy and for a reasonable dissolution rate enabling good oral bioavailability, it sets an absolute exposure limit in vivo to prevent break-down of kinase specificity in target tissues. The potency/solubility ratio, together with moderate plasma binding of about 80%, is therefore an unanticipated but absolutely central feature of compounds of the formula 1-4. This unusual safety feature of these compounds, but especially of compound 1, was illustrated by the complete absence of any signs of organ toxicity in heart, lung, kidney, liver, duodenum, and colon after 30 days of continuous treatment in all 11 animals in the HT29 xenograft study, where near maximal plasma concentrations had been maintained during the treatment course. The absence of any signs of irritation in the mucosal layers of duodenum and colon tissues, usually very sensitive to anti-cancer agents, in spite of the oral route of administration demonstrates the importance of the special physicochemical properties of compounds of the formula 1-4 for clinical utility in long-term treatment regimen.

Alternative means of tumor induction in rodents can be employed, such as chemical mutagenesis, or targeted introduction of oncogenic mutant proteins by transgenic technologies, or by using special rodent strains particularly susceptible to acquire spontaneous tumors. In any case, the treatments disclosed in this invention are equally applicable and yield similar results.

EXAMPLES

Preparation of Compounds of the Formula 1-4

Compounds with the formula 1-4 can be prepared from the compound 6 as a common precursor, which is prepared according to WO97/05140, which is incorporated herein by reference in its entirety. The lactams 1 and 2 are obtained by aminolysis of ester 6 with either methylamine or anhydrous ammonia, respectively, at elevated temperatures. As solvent dioxane or tetrahydrofurane are suitable; alternatively, methylamine or ammonia can be used as solvents themselves in pressurized vessels. Specifically in the preparation of lactame 1 and imide 3 from the corresponding esters, solid potassium cyanide can be used as a highly effective catalyst, causing the aminolysis with methylamine as reactant and solvent to occur at room temperature with minimal formation of side products, and thus improving yield and facilitating purification greatly. Many other catalysts for aminolysis of esters, like pyridine, imidazole, 4-dimethyl-amino-pyridine, etc., produced much lower yields and required more extensive purification. Also, the hydrolysis of compound 6 and subsequent amide formation with methylamine and condensing agents like carbodiimide and related agents produced only low yield. Thus another aspect of the invention is the unanticipated specificity of KCN, but not NaCN, in effecting the clean transformation of compound 6 into compound 1.

The transformation of the lactams 1 and 2 into the imides 3 and 4 can generally be achieved by oxidation with a CrO₃/pyridine complex in methylene chloride, as described in WO97/05140. Alternatively, this oxidation can also be performed with 6 prior to aminolysis.

Example 1

Conversion of 6 into Compound 1

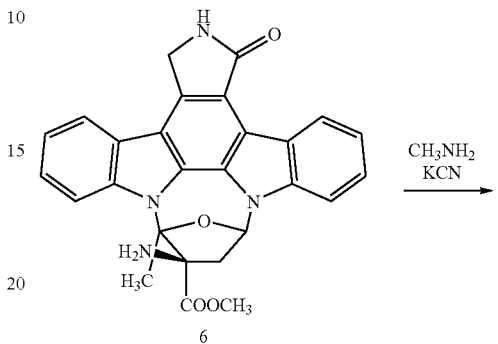

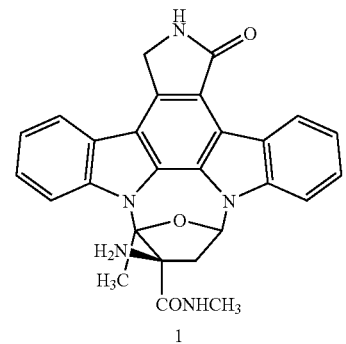

Compound 6, possessing an absolute configuration analogous to natural K252a [Fredenhagen and Peter, Tetrahedron 52, 1235-1238 (1996)], was prepared according to WO97/05140 as a methylene chloride adduct (86% in 6). A mixture of 60.5 mg (0.112 mmole) of 6 and 15 mg KCN were placed into a pressure flask, which 5 ml methyl amine were condensed into at −78° C. The mixture was dissolved by warming up to room temperature and was stirred for 110 hrs under exclusion of light, whereafter according to TLC (silica gel, methylene chloride/methanol 95:5) the starting material ($R_f$=0.28) had been completely converted into the product 1 ($R_f$=0.25). The solvent was allowed to evaporate, and the colorless solid residue was chromatographed on a 1.5×20 cm silica gel column with methylene chloride/methanol 96:4 as eluent. After evaporation of the solvent 49 mg (81%) of >99.5% ($^1$H-NMR) pure 1 was obtained.

$^1$H-NMR (300 MHz, DMSO-$d_6$): ə=1.95 (1H, dd, furanoside —CH₂—); 2.11 (3H, s, CH₃); 2.80 (3H, d, CONH—CH₃); 3.35 (1H, m, furanoside —CH₂—, partially obscured by H₂O signal); 5.01 (2H, dd, lactam —CH₂—NH—CO); 7.03 (1H, m, glycosidic —O—CH—N—); 7.27 (1H, t, arom.H); 7.38 (1H, t, arom.H); 7.49 (2H, m, arom.H); 7.85 (1H, d, arom.H); 8.07 (1H, d, arom.H); 8.23 (1H, d, arom.H); 8.32

(1H, m, CO—NH—CH$_3$); 8.64 (1H, bs, lactam —N$\underline{H}$—CO—); 9.22 (1$\underline{H}$, d, arom.$\underline{H}$). MS (ESI) m/e 466 [M+H]$^+$ Example 2

Conversion of 6 into Compound 2

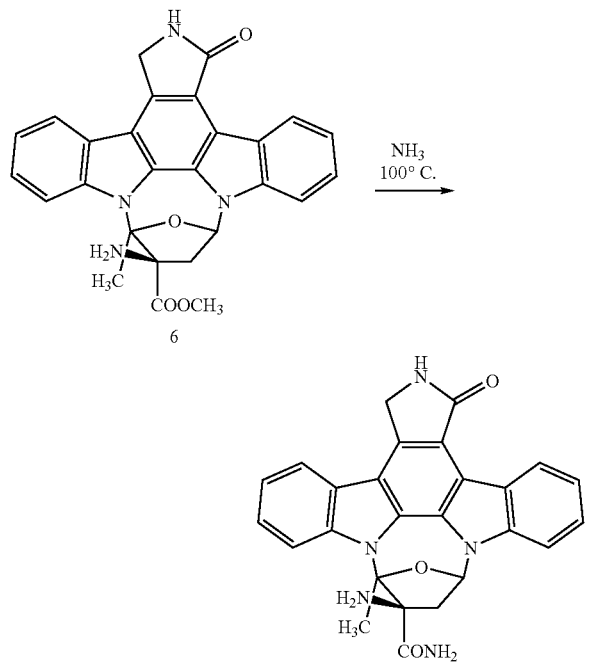

56 mg (0.103 mmole) of the solvate of 6 (86%) with methylene chloride was dissolved in 5 ml dioxane and placed into a Teflon lined pressure bomb. 5 ml of anhydrous ammonia was condensed into the vessel at −78° C. The mixture was heated in the pressure bomb under stirring to 100° C. for 24 hrs. Ammonia was allowed to evaporate slowly at room temperature, and the remaining deep yellow was solution was evaporated in vacuo to dryness. The resulting yellow solid was resuspended in a few ml methylene chloride/methanol 9:1. Undissolved material was removed by filtration, and the resulting solution was filtered through a short silica gel column with some more methylene chloride/methanol 9:1. The filtrate was evaporated in vacuo to yield 27 mg of yellow crude product, which was further purified by flash chromatography on a 1.5×20 cm silica gel column with methylene chloride/methanol 95:5 as eluent. After evaporation of the fractions containing pure product by TLC (silica gel; methylene chloride/methanol 95:5, R$_f$=0.21) 6.8 mg (14%) of ≧98% pure ($^1$H-NMR) compound 2 was obtained.

$^1$H-NMR (300 MHz, DMSO-d$_6$): ∂=1.94 (1H, dd, furanoside —C$\underline{H}_2$—); 2.20 (3H, s, CH$_3$); 3.22 (1H, m, furanoside —C$\underline{H}_2$—, partially obscured by H$_2$O signal); 5.01 (2H, dd, lactam —C$\underline{H}_2$—NH—CO); 7.03 (1H, dd, glycosidic —O—C$\underline{H}$—$\underline{N}$—); 7.27 (1H, t, arom.$\underline{H}$); 7.37 (1H, t, arom.$\underline{H}$); 7.48 (2H, m, arom.$\underline{H}$); 7.63 (1H, bs, CO—N$\underline{H}_2$); 7.79 (1H, bs, CO—N$\underline{H}_2$); 7.86 (1H, d, arom.$\underline{H}$); 8.07 (1H, d, arom.$\underline{H}$); 8.23 (1H, $\underline{d}$, arom.$\underline{H}$); 8.64 (1$\underline{H}$, bs, lactam —N$\underline{H}$—CO—); 9.21 (1H, d, arom.$\underline{H}$). MS (ESI) m/e 452 [M+H]$^+$ Biological Activity Example 3

Long-Term Growth Inhibition of MDA-MB-231 Human Breast Cancer Cells

The human estrogen receptor and EGF receptor negative MDA-MB-231 (HTB 26) breast cancer cell line (obtained from ATCC, Rockville, USA) were cultured in McCoy's 5A medium containing L-glutamine, 2.2 g/l NaHCO$_3$ and 5% fetal calf serum. Cells were maintained in a water saturated atmosphere (95% air/5% carbon dioxide) at 37° C. in 75-cm$^2$ culture flasks, and were serially passaged following trypsinization using 0.05% trypsin/0.02% EDTA.

For proliferation assays tumor cell suspensions (100 µl/well) were seeded into 96-well flat bottomed microtitration plates at a density of ca. 15 cells/microscopic field (magnification 320×). After 2-3 days the culture medium was removed by suction and replaced by fresh medium (200 µl/well) containing varying concentrations of the compound of the formula 1 or vehicle (0.5% DMSO). Compound 1 was added as 1000-fold concentrated feed solutions. On every plate 16 wells served as controls and 16 wells were used per concentration of 1. After various times of incubation the cells were fixed with glutardialdehyde and stored in a refrigerator. At the end of the assay all plates were processed simultaneously (staining with 0.02% aqueous crystal violet solution (100 µl/well). Excess dye was removed by rinsing the trays with water for 20 min. The stain bound by the cells was redissolved in 70% ethanol (180 µl/well) while shaking the microplates for about 3 hours. Absorbance (proportional to cell mass) was measured at 578 nm using a BIOTEK 309 Autoreader. The results (mean values±standard deviation) were plotted as growth curves.

Example 4

Long-Term Growth Inhibition of HT29 Human Colon Adenocarcinoma Cells

The HT29 human colon cancer cell line (obtained from ATCC, Rockville, USA) was cultured as above. Treatment with the compound of the formula 1 and analysis of growth inhibition was performed analogous to Example 3.

Example 5

Long-Term Growth Inhibition of U373 Human Astrocytoma-Glioblastoma Cells

The EGF-receptor independent U373 Human Glioblastoma cell line (obtained from ATCC, Rockville, USA) was cultured as above. Treatment with the compound of the formula 1 and analysis of growth inhibition was performed analogous to Example 3.

Example 6

Determination of Effective Dosing of Compound 1 In Vivo

Standard curves were established for the compound 1 reextracted from serum samples and brain homogenates, using the related compound 2 as internal standard. 200 µl serum samples prepared from mouse or human blood, and homogenates of 0.2 g mouse brain tissue in 0.3 ml saturated NaCl solution, were spiked with a range of concentrations of compound 1 at 10 nM, 30 nM, 100 nM, 300 nM, 1 µM, 3 µM in a mix with 500 nM of compound 2 as internal standard in DMSO (final DMSO not exceeding 2%). Serum and homogenate samples were mixed with 100 μl conc. Ammonia, and 200 μl sat'd NaCl solution was added to the serum samples. Compound 2 and internal standard 1 were reextracted twice with 2 ml ethylacetate each by vigorous vortexing for 1 min. Combined organic extracts were evaporated in a SpeedVac, and residues were taken up in 300 μl of 40% water/60% methanol (0.1% formic acid). Samples were analyzed by reversed phase HPLC on a 3.5 μM Zorbox 300SB-C8 2.1×150 mm column at 45° C. Elution was at a flow rate of 75 μl/min, isocratic for 3 min at 60:40 methanol/water (0.1% formic acid), followed by a 7 min gradient to 36:64, and a 10 min gradient to 10:90 methanol/water (0.1% formic acid). Detection was by MS/MS of fragments of 310 and 312 mass, resp., from parent molecular masses of 466 for analyte 1 and 452 for internal standard 2. Ratios were plotted as a standard curve established by linear regression. Separate linear regression fits were performed for the high (0.1-3 μM) and the low range (10-300 nM) of concentrations of 1.

Mice were dosed at 12.5 mg/kg in a vehicle of 50 mM (−)-lactic acid in 50% PEG400, and sacrificed by cardiac puncture after various time intervals. Blood collected was centrifuged for 5 min at 10,000×g at 4° C. to prepare serum, and brains were resected and divided in half for preparation of homogenates as above. Samples were spiked with 4 μl of 25 mM internal standard 2 (500 nM final) in DMSO. Reextraction was performed, and ratios of analyte 1 and internal standard 2 were determined as described above. The concentrations of compound 1 in the serum and brain samples was calculated from the standard curve.

Example 7

Determination of Free Concentrations of Compound 1 in Plasma

200 μl of human or mouse serum samples, exhaustively dialyzed into 10 mM PBS beforehand, were placed on one side of the 5 kDa cut-off membrane of a 96-well microequilibrium dialysis apparatus. 200 μl aliquots of solutions of compound 1 at 30 nM, 100 nM, 300 nM, 1 μM and 3 μM concentration in 10 mM PBS (2% DMSO) were placed on the other side. Control dialyses of serum samples were preformed against 10 mM PBS (2% DMSO) only to correct for low molecular weight fluorescent impurities of the serum samples (blank controls). To control for non-specific binding of 1 to the well and membrane materials, and for completion of equilibration, the above concentrations of 1 in 10 mM PBS (2% DMSO) were also dialyzed against 10 mM PBS only.

After 48 hrs of agitation by continuously rotating the apparatus concentrations of 1 in the control wells, assessed by fluorescence (excitation: 287 nm, emission: 375 nm), were close to equilibrium. Fluorescence in the sample wells dialyzed against serum was corrected for blank signal resulting from intrinsic fluorescence of low molecular weight components, and serum binding was assessed by comparing the loss of the corrected fluorescent signal relative to the corresponding signal of the control samples of the respective concentration against buffer only. Means of data were fitted according to a Langmuir adsorption model.

Example 8

Oral Treatment of Nude Mice with Subcutaneous Tumor Implants with the Compound 1

To establish a solid tumour 3×10⁶ tumor cells suspended in 100 μl of serum free medium (RPMI) were inoculated subcutaneously into the region of the thoracic mammary fat pads of 5 Male NMRI(nu/nu) mice of 8-10 weeks of age. After 3-4 weeks tumor bearing mice were killed by cervical dislocation and the tumor of one selected donor mouse was excised under sterile conditions. Vital tumor regions were cut into 2 mm³ pieces, picked up by a trocar (13 ga), and transplanted subcutaneously into NMRI(nu/nu) of the same stock. The tumor grade of the transplanted tissue was checked by routine histopathology (HE staining). Tumor growth and body weight were registered weekly during tumor establishment. When subcutaneous tumors reached diameters of about 3 mm the animals were randomly assigned to a treatment and a vehicle control group, each consisting of 10-12 animals, and a therapeutic regimen was started comprising twice daily applications by oral gavage of 2.5 mg/kg of compound 1 in a vehicle of 50 mM (−)-lactic acid in 50% polyethylene glycol 400. During the course of the treatment body weight changes and tumor growth were recorded three times a week. Growth curves were plotted together with standard deviations and the significance of differences was determined using an unpaired t-test in FIG. 11. In untreated mice tumor areas had grown after 9 days by about 150%, while in the treated group average tumor areas had grown only by about 50% (P=0.012). After 30 days, tumor size in treated mice was reduced by 70% (P=0.004), in the absence of any significant effect on body weight.

Other xenograft models were conducted and dosed similarly.

TABLE 1

Comparison of $IC_{50}$ values [μM] for Kinase Inhibition under Standard Conditions for 1 versus the known compound 6.

| | Kinase | |
| --- | --- | --- |
| | 1 | 6 |
| ERK2 | 0.064 | 0.87 |
| CDK1 | 0.043 | 0.65 |
| GSK3 | 1.23 | >10 |
| PKC | 1.28 | >10 |
| PKA | 0.30 | >10 |

TABLE 2

Comparison of $IC_{50}$ values [μM] for Kinase Inhibition under Standard Conditions for 1 versus Relevant Known Compounds based on Scaffold 10.

| | Kinase | | | |
| --- | --- | --- | --- | --- |
| | | 7 | 8 | 9 |
| | | Substituents in Scaffold 10 | | |
| | | X: —NH₂ | —OH | —OH |
| | 1 | Z: H,H | =O | H,H |
| ERK2 | 0.064 | 0.60 | 0.12 | 0.48 |
| CDK1 | 0.043 | 0.18 | 0.063 | 0.11 |
| GSK3 | 1.23 | 0.35 | 0.037 | 0.40 |
| PKC | 1.28 | 0.26 | 0.12 | 0.21 |
| PKA | 0.30 | 0.44 | 0.078 | 0.55 |

TABLE 3

Summary of Results with Compound 1 in Various Mouse Xenograft Models

| Xenograft | Tissue Origin | Genotype | N Treated/ N Vehicle | Mean % Inhibition | N tumors with no/ neg. growth |
|---|---|---|---|---|---|
| NCI-H23 | Lung | Ras/p53 | 10/10 | 92% | 5 of 10 |
| HT29 | Colon | Raf/PI3K/ p53/APC | 11/10 | 70% | 2 of 11 |
| U251 | Brain | CDKN2A/ p53/PTEN | 11/12 | 74% | 3 of 11 |
| SK-MEL-5 | Melanoma | Raf/ CDKN2A | 10/11 | 122% | 7 of 10 |
| OVCAR-3 | Ovarian | p53 | 11/12 | 78% | 4 of 11 |
| ACHN | Kidney | CDKN2A | 10/10 | 86% | 5 of 10 |
| PC-3 | Prostate | p53/PTEN | 11/11 | 68% | 2 of 11 |
| T-47D | Breast | p53/PI3K | 10/11 | 81% | 4 of 10 |

The invention claimed is:

1. A method of treating tumors expressing elevated levels of an activated kinase pathway in a subject in need of such treatment, wherein the activated kinase pathway is extracellulular signal regulated kinase (ERK), comprising administering to said subject an effective amount of a compound of Formula 1:

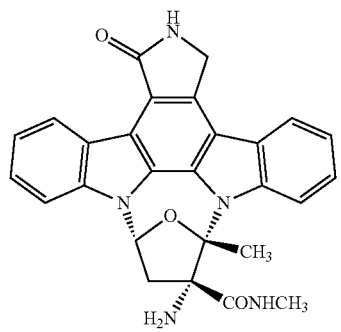

or a pharmaceutically acceptable salt thereof.

2. A method of inhibiting an activated kinase pathway in a subject in need of such treatment comprising administering to said subject an effective amount of a compound of Formula 1:

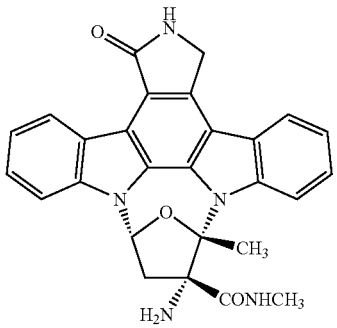

or a pharmaceutically acceptable salt thereof.

3. A method of treating cancer in a subject in need of such treatment comprising administering to said subject an effective amount of a compound of Formula 1:

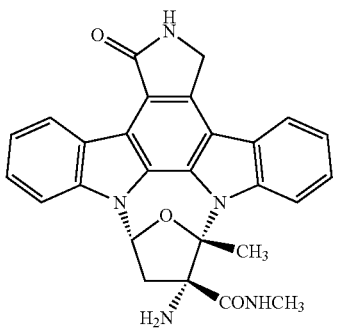

or a pharmaceutically acceptable salt thereof.

4. The method of claim 3, wherein the cancer is selected from the group consisting of: breast cancers, colon cancers, gliomas, melanomas, prostate cancers, ovarian cancers, bladder cancers, head and neck cancers, epidermal cancers, pancreatic cancers, lung cancers, myeloid leukemias, thyroid follicular tumors, myelodysplastic syndrome, non-Hodgkin's lymphomas, and multiple myelomas.

5. The method of claim 3, wherein the cancer is selected from the group consisting of lung cancer, colon cancer, brain cancer, melanoma, ovarian cancer, kidney cancer, prostate cancer and breast cancer.

6. The method of claim 3, wherein said cancer is breast cancer, colon cancer, or glioma.

7. The method of claim 3, wherein the cancer is related to activation of a MAP protein kinase as a result of an oncogenic mutation in a gene encoding a cell surface receptor tyrosine kinase (RTK) or other upstream signaling protein, wherein said other upstream signaling protein is a Raf or Ras protein, and wherein said MAP protein kinase is an extracellular regulatory kinase-2 (ERK-2) and/or an extracellular regulatory kinase-1 (ERK-1).

* * * * *